United States Patent
Bakke

(10) Patent No.: US 9,573,821 B2
(45) Date of Patent: Feb. 21, 2017

(54) METHODS TO RECOVER CESIUM FORMATE FROM A MIXED ALKALI METAL FORMATE BLEND

(71) Applicant: Cabot Corporation, Boston, MA (US)

(72) Inventor: Bart F. Bakke, The Woodlands, TX (US)

(73) Assignee: Cabot Corporation, Boston, MA (US)

( * ) Notice: Subject to any disclaimer, the term of this patent is extended or adjusted under 35 U.S.C. 154(b) by 0 days.

(21) Appl. No.: 15/244,095

(22) Filed: Aug. 23, 2016

(65) Prior Publication Data

US 2016/0355406 A1 Dec. 8, 2016

Related U.S. Application Data

(62) Division of application No. 14/549,926, filed on Nov. 21, 2014, now Pat. No. 9,452,966.

(60) Provisional application No. 61/910,976, filed on Dec. 3, 2013.

(51) Int. Cl.

| | |
|---|---|
| *C01D 17/00* | (2006.01) |
| *C07C 51/02* | (2006.01) |
| *C07C 51/43* | (2006.01) |
| *C22B 26/10* | (2006.01) |
| *C09K 8/05* | (2006.01) |
| *C07C 51/487* | (2006.01) |
| *C22B 3/44* | (2006.01) |
| *C01D 5/06* | (2006.01) |
| *C22B 3/46* | (2006.01) |

(52) U.S. Cl.
CPC ............ *C01D 17/003* (2013.01); *C01D 5/06* (2013.01); *C01D 17/00* (2013.01); *C07C 51/02* (2013.01); *C07C 51/43* (2013.01); *C07C 51/487* (2013.01); *C09K 8/05* (2013.01); *C22B 3/44* (2013.01); *C22B 3/46* (2013.01); *C22B 26/10* (2013.01); *C09K 2208/00* (2013.01)

(58) Field of Classification Search
CPC .................................................... C01D 17/003
See application file for complete search history.

(56) References Cited

U.S. PATENT DOCUMENTS

| | | | | |
|---|---|---|---|---|
| 3,207,571 | A | * | 9/1965 | Berthold ............... C01D 17/00 423/202 |
| RE32,556 | E | | 12/1987 | Mein |
| 5,900,221 | A | | 5/1999 | Hofmann et al. |
| 6,015,535 | A | | 1/2000 | Brown et al. |
| 6,436,879 | B1 | | 8/2002 | Brown et al. |
| 6,652,820 | B2 | * | 11/2003 | Bakke .................... C01D 1/20 423/179 |
| 6,818,595 | B2 | | 11/2004 | Benton et al. |
| 7,323,150 | B2 | | 1/2008 | Bakke et al. |
| 7,759,273 | B2 | | 7/2010 | Bakke |
| 2002/0143209 | A1 | | 10/2002 | Bakke |
| 2006/0009649 | A1 | | 1/2006 | Murray et al. |
| 2006/0239900 | A1 | | 10/2006 | Bakke |
| 2015/0152033 | A1 | | 6/2015 | Bakke |

FOREIGN PATENT DOCUMENTS

| | | |
|---|---|---|
| DE | 2651228 A1 | 5/1978 |
| EP | 0572113 A1 | 12/1993 |
| WO | 9631435 A1 | 10/1996 |

OTHER PUBLICATIONS

Brine Density and PVT Data, Cabot Specialty Fluids, Formate Technical Manual, Version 9, Section A2, Jan. 2013, pp. 1-39.
International Search Report and Written Opinion issued in corresponding International Application No. PCT/US2013/076445, dated Nov. 13, 2014 (18 pages).

* cited by examiner

*Primary Examiner* — Paul A Zucker

(57) ABSTRACT

Methods to recover or separate cesium formate or rubidium formate or both from a mixed alkali metal formate blend are described. One method involves adding cesium sulfate or rubidium sulfate to the mixed alkali metal formate blend in order to preferentially precipitate potassium sulfate from the mixed alkali metal formate blend. Another method involves adding cesium carbonate or cesium bicarbonate or both to preferentially precipitate potassium carbonate/bicarbonate and/or other non-cesium or non-rubidium metals from the mixed alkali metal blend. Further optional steps are also described. Still one other method involves converting cesium sulfate to cesium hydroxide.

21 Claims, 7 Drawing Sheets

FIG 1

| | METRIC | | | | | | | | Quantities for 1 m³ brine | |
|---|---|---|---|---|---|---|---|---|---|---|
| Density | KFo brine | CsFo brine | KFo | CsFo | H₂O | K⁺ | Cs⁺ | HCOO- | KFo | CsFo |
| [g/cm³] | [%wt] | [%wt] | [%wt] | [%wt] | [%wt] | [mol/L] | [mol/L] | [mol/L] | [liter] | [liter] |
| 1.57 | 100.00 | 0.00 | 75.0 | 0.0 | 25.0 | 14.0 | 0.0 | 14.0 | 1,000.0 | 0.0 |
| 1.58 | 97.79 | 2.21 | 73.4 | 1.8 | 24.9 | 13.8 | 0.2 | 13.9 | 984.1 | 15.9 |
| 1.59 | 95.61 | 4.39 | 71.7 | 3.5 | 24.8 | 13.6 | 0.3 | 13.9 | 968.3 | 31.7 |
| 1.60 | 93.45 | 6.55 | 70.1 | 5.2 | 24.7 | 13.3 | 0.5 | 13.8 | 952.4 | 47.6 |
| 1.61 | 91.32 | 8.68 | 68.5 | 6.9 | 24.6 | 13.1 | 0.6 | 13.7 | 936.5 | 63.5 |
| 1.62 | 89.22 | 10.78 | 66.9 | 8.6 | 24.5 | 12.9 | 0.8 | 13.7 | 920.6 | 79.4 |
| 1.63 | 87.15 | 12.85 | 65.4 | 10.3 | 24.3 | 12.7 | 0.9 | 13.6 | 904.8 | 95.2 |
| 1.64 | 85.09 | 14.91 | 63.8 | 11.9 | 24.2 | 12.4 | 1.1 | 13.5 | 888.9 | 111.1 |
| 1.65 | 83.07 | 16.93 | 62.3 | 13.5 | 24.1 | 12.2 | 1.3 | 13.5 | 873.0 | 127.0 |
| 1.66 | 81.07 | 18.93 | 60.8 | 15.1 | 24.0 | 12.0 | 1.4 | 13.4 | 857.1 | 142.9 |
| 1.67 | 79.09 | 20.91 | 59.3 | 16.7 | 24.0 | 11.8 | 1.6 | 13.3 | 841.3 | 158.7 |
| 1.68 | 77.14 | 22.86 | 57.9 | 18.3 | 23.9 | 11.6 | 1.7 | 13.3 | 825.4 | 174.6 |
| 1.69 | 75.20 | 24.80 | 56.4 | 19.8 | 23.8 | 11.3 | 1.9 | 13.2 | 809.5 | 190.5 |
| 1.70 | 73.30 | 26.70 | 55.0 | 21.3 | 23.7 | 11.1 | 2.0 | 13.2 | 793.7 | 206.3 |
| 1.71 | 71.41 | 28.59 | 53.6 | 22.9 | 23.6 | 10.9 | 2.2 | 13.1 | 777.8 | 222.2 |
| 1.72 | 69.55 | 30.45 | 52.2 | 24.3 | 23.5 | 10.7 | 2.4 | 13.0 | 761.9 | 238.1 |
| 1.73 | 67.70 | 32.30 | 50.8 | 25.8 | 23.4 | 10.4 | 2.5 | 13.0 | 746.0 | 254.0 |
| 1.74 | 65.88 | 34.12 | 49.4 | 27.3 | 23.3 | 10.2 | 2.7 | 12.9 | 730.2 | 269.8 |
| 1.75 | 64.08 | 35.92 | 48.1 | 28.7 | 23.2 | 10.0 | 2.8 | 12.8 | 714.3 | 285.7 |
| 1.76 | 62.30 | 37.70 | 46.7 | 30.1 | 23.1 | 9.8 | 3.0 | 12.8 | 698.4 | 301.6 |
| 1.77 | 60.54 | 39.46 | 45.4 | 31.5 | 23.0 | 9.6 | 3.1 | 12.7 | 682.5 | 317.5 |
| 1.78 | 58.80 | 41.20 | 44.1 | 32.9 | 23.0 | 9.3 | 3.3 | 12.6 | 666.7 | 333.3 |
| 1.79 | 57.08 | 42.92 | 42.8 | 34.3 | 22.9 | 9.1 | 3.5 | 12.6 | 650.8 | 349.2 |
| 1.80 | 55.38 | 44.62 | 41.5 | 35.7 | 22.8 | 8.9 | 3.6 | 12.5 | 634.9 | 365.1 |
| 1.81 | 53.70 | 46.30 | 40.3 | 37.0 | 22.7 | 8.7 | 3.8 | 12.4 | 619.0 | 381.0 |
| 1.82 | 52.03 | 47.97 | 39.0 | 38.4 | 22.6 | 8.4 | 3.9 | 12.4 | 603.2 | 396.8 |
| 1.83 | 50.39 | 49.61 | 37.8 | 39.7 | 22.5 | 8.2 | 4.1 | 12.3 | 587.3 | 412.7 |
| 1.84 | 48.76 | 51.24 | 36.6 | 41.0 | 22.5 | 8.0 | 4.2 | 12.2 | 571.4 | 428.6 |
| 1.85 | 47.15 | 52.85 | 35.4 | 42.3 | 22.4 | 7.8 | 4.4 | 12.2 | 555.6 | 444.4 |
| 1.86 | 45.55 | 54.45 | 34.2 | 43.5 | 22.3 | 7.6 | 4.6 | 12.1 | 539.7 | 460.3 |
| 1.87 | 43.98 | 56.02 | 33.0 | 44.8 | 22.2 | 7.3 | 4.7 | 12.0 | 523.8 | 476.2 |
| 1.88 | 42.42 | 57.58 | 31.8 | 46.0 | 22.1 | 7.1 | 4.9 | 12.0 | 507.9 | 492.1 |
| 1.89 | 40.88 | 59.12 | 30.7 | 47.3 | 22.1 | 6.9 | 5.0 | 11.9 | 492.1 | 507.9 |
| 1.90 | 39.35 | 60.65 | 29.5 | 48.5 | 22.0 | 6.7 | 5.2 | 11.8 | 476.2 | 523.8 |
| 1.91 | 37.84 | 62.16 | 28.4 | 49.7 | 21.9 | 6.4 | 5.3 | 11.8 | 460.3 | 539.7 |
| 1.92 | 36.34 | 63.66 | 27.3 | 50.9 | 21.8 | 6.2 | 5.5 | 11.7 | 444.4 | 555.6 |
| 1.93 | 34.86 | 65.14 | 26.2 | 52.1 | 21.8 | 6.0 | 5.6 | 11.6 | 428.6 | 571.4 |
| 1.94 | 33.40 | 66.60 | 25.1 | 53.2 | 21.7 | 5.8 | 5.8 | 11.6 | 412.7 | 587.3 |
| 1.95 | 31.95 | 68.05 | 24.0 | 54.4 | 21.6 | 5.6 | 6.0 | 11.5 | 396.8 | 603.2 |
| 1.96 | 30.52 | 69.48 | 22.9 | 55.6 | 21.6 | 5.3 | 6.1 | 11.5 | 381.0 | 619.0 |
| 1.97 | 29.10 | 70.90 | 21.8 | 56.7 | 21.5 | 5.1 | 6.3 | 11.4 | 365.1 | 634.9 |
| 1.98 | 27.69 | 72.31 | 20.8 | 57.8 | 21.4 | 4.9 | 6.4 | 11.3 | 349.2 | 650.8 |
| 1.99 | 26.30 | 73.70 | 19.7 | 58.9 | 21.3 | 4.7 | 6.6 | 11.3 | 333.3 | 666.7 |
| 2.00 | 24.92 | 75.08 | 18.7 | 60.0 | 21.3 | 4.4 | 6.7 | 11.2 | 317.5 | 682.5 |
| 2.01 | 23.56 | 76.44 | 17.7 | 61.1 | 21.2 | 4.2 | 6.9 | 11.1 | 301.6 | 698.4 |
| 2.02 | 22.21 | 77.79 | 16.7 | 62.2 | 21.1 | 4.0 | 7.1 | 11.1 | 285.7 | 714.3 |
| 2.03 | 20.87 | 79.13 | 15.7 | 63.3 | 21.1 | 3.8 | 7.2 | 11.0 | 269.8 | 730.2 |
| 2.04 | 19.55 | 80.45 | 14.7 | 64.3 | 21.0 | 3.6 | 7.4 | 10.9 | 254.0 | 746.0 |
| 2.05 | 18.23 | 81.77 | 13.7 | 65.4 | 20.9 | 3.3 | 7.5 | 10.9 | 238.1 | 761.9 |
| 2.06 | 16.94 | 83.06 | 12.7 | 66.4 | 20.9 | 3.1 | 7.7 | 10.8 | 222.2 | 777.8 |
| 2.07 | 15.65 | 84.35 | 11.7 | 67.4 | 20.8 | 2.9 | 7.8 | 10.7 | 206.3 | 793.7 |
| 2.08 | 14.38 | 85.62 | 10.8 | 68.5 | 20.8 | 2.7 | 8.0 | 10.7 | 190.5 | 809.5 |
| 2.09 | 13.12 | 86.88 | 9.8 | 69.5 | 20.7 | 2.4 | 8.2 | 10.6 | 174.6 | 825.4 |
| 2.10 | 11.87 | 88.13 | 8.9 | 70.5 | 20.6 | 2.2 | 8.3 | 10.5 | 158.7 | 841.3 |
| 2.11 | 10.63 | 89.37 | 8.0 | 71.5 | 20.6 | 2.0 | 8.5 | 10.5 | 142.9 | 857.1 |
| 2.12 | 9.40 | 90.60 | 7.1 | 72.4 | 20.5 | 1.8 | 8.6 | 10.4 | 127.0 | 873.0 |
| 2.13 | 8.19 | 91.81 | 6.1 | 73.4 | 20.5 | 1.6 | 8.8 | 10.3 | 111.1 | 888.9 |
| 2.14 | 6.99 | 93.01 | 5.2 | 74.4 | 20.4 | 1.3 | 8.9 | 10.3 | 95.2 | 904.8 |
| 2.15 | 5.80 | 94.20 | 4.3 | 75.3 | 20.3 | 1.1 | 9.1 | 10.2 | 79.4 | 920.6 |
| 2.16 | 4.61 | 95.39 | 3.5 | 76.3 | 20.3 | 0.9 | 9.3 | 10.1 | 63.5 | 936.5 |
| 2.17 | 3.45 | 96.55 | 2.6 | 77.2 | 20.2 | 0.7 | 9.4 | 10.1 | 47.6 | 952.4 |
| 2.18 | 2.29 | 97.71 | 1.7 | 78.1 | 20.2 | 0.4 | 9.6 | 10.0 | 31.7 | 968.3 |
| 2.19 | 1.14 | 98.86 | 0.9 | 79.0 | 20.1 | 0.2 | 9.7 | 10.0 | 15.9 | 984.1 |
| 2.20 | 0.00 | 100.00 | 0.0 | 80.0 | 20.0 | 0.0 | 9.9 | 9.9 | 0.0 | 1,000.0 |

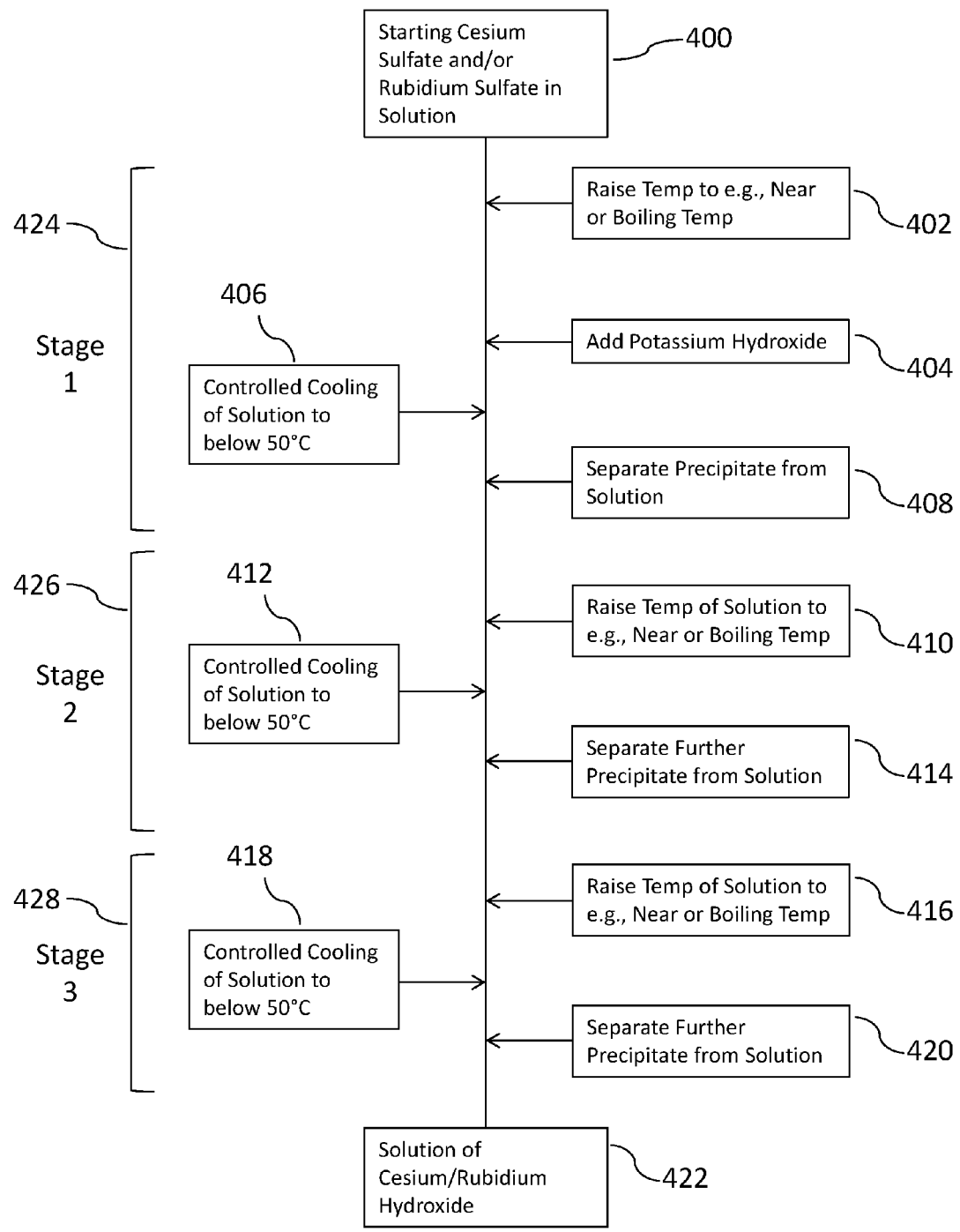

METHODS TO RECOVER CESIUM FORMATE FROM A MIXED ALKALI METAL FORMATE BLEND

RELATED APPLICATION

This application is a divisional of U.S. patent application Ser. No. 14/549,926, filed Nov. 21, 2014, which claims priority under 35 U.S.C. §119(e) from U.S. Prov. Appl. No. 61/910,976, filed Dec. 3, 2013, the disclosures of which are incorporated herein by reference.

BACKGROUND OF THE INVENTION

The present invention relates to the recovery of cesium formate and/or rubidium formate from a mixed alkali metal formate blend that is in solution.

Cesium formate solutions, such as cesium formate brines, are a high-density, low-viscosity clear brines that are quite useful as drilling fluids, completion fluids, intervention fluids, and suspension fluids in the oil and gas field recovery operations in wells and reservoirs. Cesium formate is quite useful in HPHT (high pressure high temperature) drilling sites. While cesium formate has a density or specific gravity of 2.2 to 2.4 s.g., many times there is a need to formulate a specific gravity or density that is below the specific gravity for a pure cesium formate brine based on the particular demands and needs of the particular well site. When a lower specific gravity or density is required, many times potassium formate, which has a lower density, is used to reduce the overall density of the brine or fluid. By using various ratios of cesium formate to potassium formate, a wide range of specific gravities are achievable, such as 1.57 to 2.3 s.g. The potassium formate is fully miscible with the cesium formate, thus making it a useful blend for oil and gas recovery efforts. Thus, when cesium formate solution, such as cesium formate brine, is commercially supplied to end users, such as drilling rigs, each well will have a unique need with regard to the density of fluid to use and, therefore, individual specialized blends are created to achieve a very specific density of fluid by using, typically, cesium formate in combination with potassium formate, though other formates, such as sodium formate and lithium formate, may be used, though to a far lesser extent. When the particular use of the brine or fluid is completed, many times the brine or fluid is recovered to the extent possible due to its value, and then sent back to the supplier.

However, this individual need for specialized blends per drilling site results in a large inventory of different returned individual blends from each well site. For instance, one blend may be 1.6 s.g. and another blend used in another well site may be 1.7 s.g. and another blend used at a further well site might be 1.8 s.g. and so on. This results in hundreds and hundreds of liters of different blends. Since these blends are not discarded due to their valuable components of cesium formate and, to a lesser extent, potassium formate, their re-use in subsequent drilling sites would be very desirable. However, because cesium formate and potassium formate are totally miscible with each other and cannot be physically separated based on density or simple separation techniques, this creates a problem with regard to their subsequent use. Further, as indicated, the fact that each blend is individualized for a particular well site makes it quite difficult to provide this blend to a subsequent user unless their density demands (and amounts) are identical with the blend that is in inventory. Generally, when an individualized density brine is created, one starts from the highest density which is essentially a pure or nearly almost pure and nearly saturated cesium formate solution, which is 2.2 to 2.4 s.g. at 25° C., and then using potassium formate, the density is reduced to desired needs. Thus, the most efficient way to dial-in a density is to start with cesium formate and then to lower the density using potassium formate. Since many of the blends returned to the supplier/formulator after use are of varying amounts with regard to cesium formate and potassium formate, and because the cesium formate cannot be separated by basic physical separation techniques, this creates a large inventory of rather unuseful blends. Essentially, what is needed is to return the components to their near individual state or, in other words, substantially separate the blend into its individual formate components so that the starting cesium formate can again be used as the starting point and then adjust the density of the formate solution using potassium formate or other formates to desirable densities. Having a standard starting material, such as cesium formate or almost pure cesium formate solution or brine, with a standard known density range permits one to create a single usable inventory that can then be used and adjusted per individual well needs.

Accordingly, there is a need in the industry to provide cost-efficient, yield-efficient, and/or effective methods to separate a mixed alkali metal formate blend so as to recover and restore the cesium formate and potassium formate (and/or other formates) from the mixed alkali metal formate blend for subsequent use.

SUMMARY OF THE PRESENT INVENTION

A feature of the present invention is to provide methods to separate, recover, and/or restore cesium formate from a mixed alkali metal formate blend in solution.

A further feature of the present invention is to separate, recover, and/or restore cesium formate or rubidium formate or both from a mixed alkali metal formate blend in solution.

A further feature of the present invention is to separate, recover, and/or restore cesium formate or rubidium formate or both from a mixed alkali metal formate blend in solution, where the solution contains cesium formate or rubidium formate or both and also contains potassium formate, sodium formate, or lithium formate, or any combination thereof.

An additional feature of the present invention is to provide an efficient and inexpensive process to convert cesium sulfate to cesium hydroxide and/or convert rubidium sulfate to rubidium hydroxide.

Additional features and advantages of the present invention will be set forth in part in the description that follows, and in part will be apparent from the description, or may be learned by practice of the present invention. The features and advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method to separate, recover, and/or restore at least a portion of cesium formate from a mixed metal alkali metal formate blend in solution. This solution contains at least cesium formate and potassium formate. The method includes adding cesium sulfate to the mixed alkali metal formate blend to form at least potassium sulfate precipitate and additional cesium formate in solution. The alkali metal formate blend can optionally be at a temperature of at least 50° C. or can be raised to a temperature of at least 50° C. so as to preferentially precipitate potassium sulfate and form additional cesium formate in solution. This method then includes separating the potassium sulfate precipitate (or a portion thereof) from the solution to obtain a purified solution.

The present invention further relates to a method to recover cesium formate or rubidium formate or both from a mixed alkali metal formate blend in solution. The alkali metal formate blend contains at least Component 1) cesium formate or rubidium formate or both, and Component 2) potassium formate or sodium formate or lithium formate, or any combination thereof. The method includes adding cesium sulfate and/or rubidium sulfate to the mixed alkali metal formate blend to form an alkali metal sulfate precipitate (preferably other than cesium sulfate and/or rubidium sulfate) and additional cesium formate or rubidium formate or both in the solution. The alkali metal formate blend can be optionally at a temperature of at least 50° C. or can be raised to a temperature of at least 50° C. so as to preferentially precipitate an alkali metal sulfate precipitate (other than cesium sulfate and/or rubidium sulfate) and form additional cesium formate or rubidium formate or both in the solution. The method then includes separating at least a portion of the alkali metal sulfate precipitate from the solution to obtain a purified solution.

The present invention also relates to a method to recover cesium formate from a mixed metal alkali formate blend in solution that contains at least cesium formate and potassium formate. In this method, the method involves adding cesium carbonate or cesium bicarbonate or both to the mixed alkali metal formate blend so as to form at least potassium carbonate and/or potassium bicarbonate and additionally form cesium formate in solution. The alkali metal formate blend can optionally be at a temperature of or can be raised to a temperature of at least 50° C. so as to preferentially precipitate potassium carbonate precipitate and/or potassium bicarbonate precipitate (depending upon the added cesium component) and additionally form cesium formate in the solution. The method then involves separating at least a portion of the potassium carbonate precipitate and/or potassium bicarbonate precipitate from the solution to obtain a purified solution.

The present invention further relates to a method to recover at least a portion of cesium formate or rubidium formate or both from a mixed alkali metal formate blend in solution. The mixed alkali metal formate blend in solution includes at least Component 1) cesium formate or rubidium formate or both and also contains Component 2) potassium formate, lithium formate, or sodium formate or any combination thereof. This method includes adding cesium carbonate, cesium bicarbonate, rubidium carbonate, rubidium bicarbonate, or any combinations thereof, to the mixed alkali metal formate blend to form an alkali metal carbonate or alkali metal bicarbonate precipitate (depending upon the cesium/rubidium component added) and additional cesium formate, rubidium formate, or both in the solution. The alkali metal carbonate precipitate and/or alkali metal bicarbonate precipitate would not primarily be cesium carbonate, cesium bicarbonate, rubidium carbonate, and/or rubidium bicarbonate. The alkali metal formate blend can be optionally at a temperature of or can be raised to a temperature of at least 50° C. so as to preferentially precipitate an alkali metal carbonate precipitate (other than a cesium and/or rubidium carbonate) or alkali metal bicarbonate precipitate (other than a cesium and/or rubidium bicarbonate) (depending upon the cesium/rubidium component that was added) and form additional cesium formate, rubidium formate, or both in the solution. The method then involves separating at least a portion of the alkali metal carbonate precipitate and/or alkali metal bicarbonate precipitate from the solution to obtain a purified solution.

Furthermore, the present invention relates to a method to convert cesium sulfate (for instance in solution) to cesium hydroxide (CsOH) (for instance in solution) and/or to convert rubidium sulfate (for instance in solution) to rubidium hydroxide (RbOH). The method includes adding potassium hydroxide (KOH) to the cesium sulfate (and/or rubidium sulfate) to form cesium hydroxide (and/or rubidium hydroxide), preferably in solution, and potassium sulfate (preferably potassium sulfate precipitate). The cesium sulfate or cesium sulfate solution (and/or rubidium sulfate or rubidium sulfate solution) can optionally be at a temperature of at least 50° C. or can be raised to a temperature of at least 50° C. so as to preferentially precipitate potassium sulfate precipitate and form cesium hydroxide (and/or rubidium hydroxide) in solution. This method then includes separating the potassium sulfate precipitate (or a portion thereof) from the solution to obtain a solution of cesium hydroxide (and/or rubidium hydroxide). This method can be used alone or combined with the other methods described herein (for instance, to manipulate the pH of the mixed brine solution). For instance, the KOH can be added before, at the same time, or after a) the addition of cesium sulfate and/or rubidium sulfate or b) the addition of cesium carbonate and/or cesium bicarbonate and/or rubidium carbonate and/or rubidium bicarbonate in those methods described herein.

In lieu of or in addition to cesium sulfate, as an option rubidium sulfate can be used, wherein the potassium hydroxide is added to the rubidium sulfate to form rubidium hydroxide.

It is to be understood that both the foregoing general description and the following detailed description are exemplary and explanatory only and are intended to provide a further explanation of the present invention, as claimed. It is further understood that the various methods and/or techniques can be combined and otherwise used together in any fashion to achieve the goals of the present invention.

The accompanying drawings, which are incorporated in and constitute a part of this application, illustrate some of the features of the present invention and together with the description, serve to explain the principles of the present invention.

BRIEF DESCRIPTION OF DRAWINGS

FIG. 1 is a table showing various blending ratios between potassium formate and cesium formate to achieve a variety of different densities.

FIGS. 6 and 7 are flow charts showing examples of steps and optional steps that can be utilized in the present invention to obtain cesium hydroxide and/or rubidium hydroxide from cesium sulfate and/or rubidium sulfate.

DETAILED DESCRIPTION OF THE PRESENT INVENTION

Figure 2:
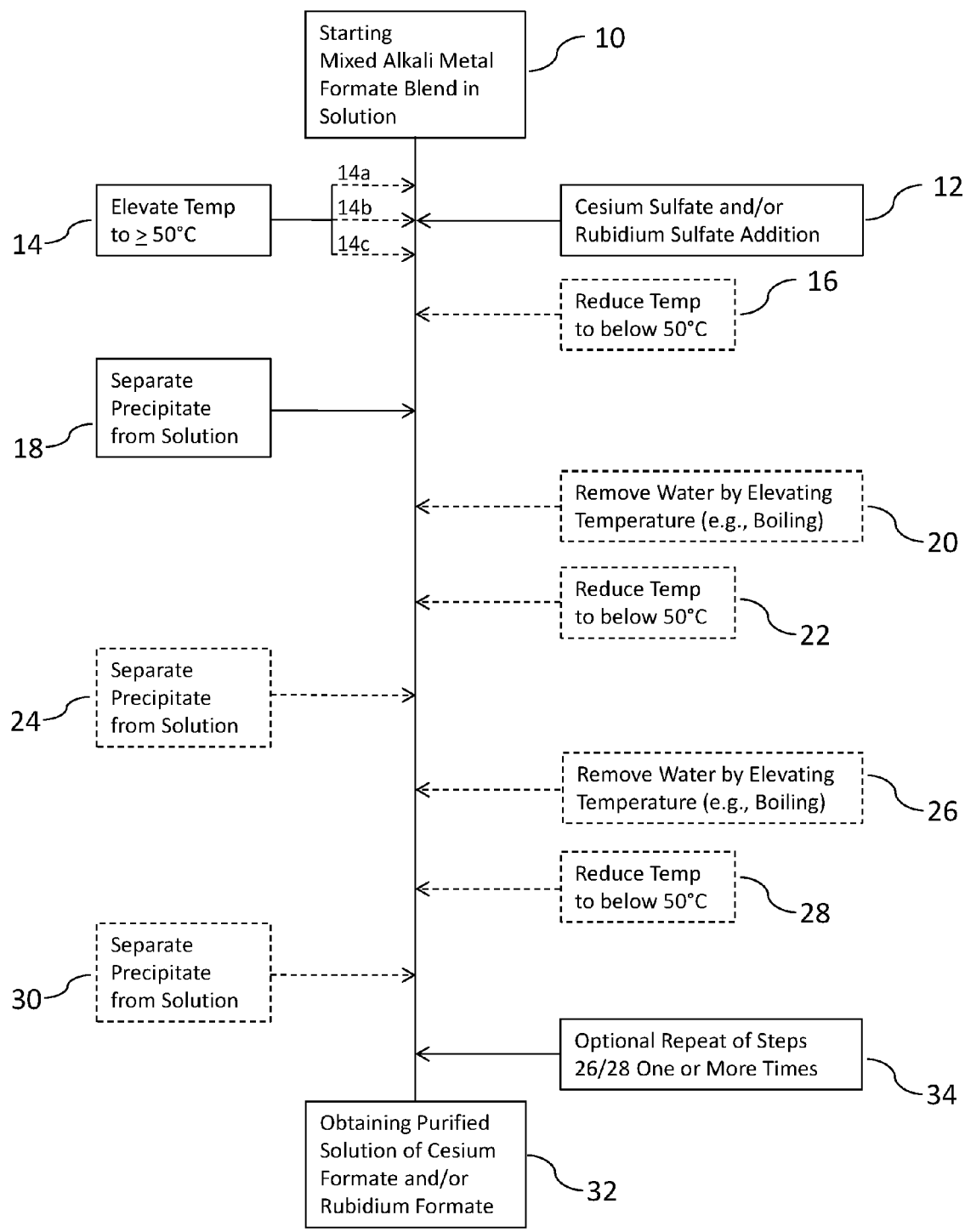
FIGS. 2-5 are flow charts showing examples of steps and optional steps that can be utilized in the present invention to obtain cesium formate and/or rubidium formate from a mixed alkali metal formate blend.

The present invention relates to methods to recover at least a portion of a particular alkali metal formate, such as cesium formate and/or rubidium formate, from a mixed alkali metal formate blend that is in solution. More specifically and just as an example, the present invention relates to methods to recover at least a portion of cesium formate from a mixed alkali metal formate blend in solution, where the solution contains at least cesium formate and potassium formate.

For purposes of the present invention, the various embodiments of the present invention relate to methods to recover or separate or otherwise purify cesium formate, rubidium formate or both that are present in a mixed alkali metal formate blend in solution (which can be considered the starting blend). By using one or more methods of the present invention, a cesium formate and/or rubidium formate solution of high purity or higher purity can be obtained, whereas the majority of the alkali metal formates that are not cesium formate or rubidium formate can be removed or otherwise separated from the blend (e.g., over 50 wt % over 75 wt %, over 85 wt % over 95 wt %, or 75 wt % to 100 wt % or 85 wt % to 99 wt % are removed based on the weight of non-cesium and non-rubidium formates).

With regard to the formate solution that is treated by the methods of the present invention, the formate-containing solution is or can be nearly or fully saturated with regard to the formate salts. For instance, at a s.g. of about 1.57, which would mean that the formates are primarily potassium formates, a fully saturated formate solution would be where the water content is a maximum of about 25 wt % water with regard to the overall weight of the formate solution. At a s.g. of about 2.3, this would mean that the solution is primarily a cesium formate-containing solution and a near or fully saturated solution for this type of s.g. would be about 16 wt % water. Thus, a nearly or fully saturated formate solution that contains potassium formate with cesium formate and, optionally, rubidium formate or other alkali metal formates, can typically range from about 16 wt % to about 25 wt % water based on the overall weight of the formate-containing solution.

As just one example of the present invention, a method to recover or separate at least a portion of cesium formate from a mixed alkali metal formate blend is described. The mixed alkali metal formate blend is in solution and contains at least cesium formate and potassium formate. The method includes adding cesium sulfate to the mixed alkali metal formate blend so as to react the cesium sulfate with the potassium formate and form a potassium sulfate precipitate and additionally form cesium formate. As an option, the mixed alkali metal formate blend prior to, during, or after the addition of the cesium formate can be at a temperature of at least 50° C. or raised to a temperature of at least 50° C. so as to preferentially precipitate potassium sulfate, as well as form additional cesium formate in solution. The method then involves separating at least a portion of the potassium sulfate precipitate from the solution to obtain a purified solution.

In more detail, for any of the methods of the present invention, the mixed metal alkali metal formate blend in solution can contain from about 1 wt % to about 99 wt % cesium formate and from about 99 wt % to about 1 wt % potassium formate based on the weight of the metal alkali metal formates present in the blend. For example, the mixed alkali metal formate blend in solution can contain from about 20 wt % to about 60 wt % cesium formate and from about 80 wt % to about 40 wt % potassium formate or from about 30 wt % to about 45 wt % cesium formate and from about 70 wt % to about 55 wt % percent potassium formate, based on the weight of the alkali metal formates present in the blend. For example, FIG. 1 provides various wt % for each formate that can be found in the mixed blends.

With regard to adding the cesium sulfate to the mixed alkali metal formate blend, the cesium sulfate can be any commercially-available grade of cesium sulfate. The cesium sulfate is commercially available from Cabot Corporation, and can be used in powder form or in solution form. When in solution form, for instance, the solution can be a 50 wt % to 64 wt % cesium sulfate solution. Preferably, though optional, the cesium sulfate is of high purity, such as about 90 wt % or higher, or 95 wt % or higher (e.g., 95% to 99.999%) pure cesium sulfate (on a dry salt basis). The cesium sulfate can be added in any form, such as a powder or liquid. The amount of cesium sulfate added to the mixed alkali metal formate blend is dependent upon the amount of potassium formate present in the mixed alkali metal formate blend. Generally, the amount of the cesium sulfate added is an amount that reacts with some, most, or all of the potassium that is from the potassium formate so as to form a potassium sulfate, and preferably without any excess cesium sulfate remaining or an amount below 5 wt % or below 1 wt % cesium sulfate based on the weight of solution. The amount can be an amount that reacts with some, most, or all of the potassium, sodium, and/or lithium that is present in formate form so as to form their respective sulfate salt and fall out as precipitates. Thus, ideally, the amount of cesium sulfate introduced is preferably an amount that reacts with the potassium formate and preferably is used up in the reaction that forms the potassium sulfate precipitate. For instance, the cesium sulfate can be added in an amount to react with from about 10 wt % to about 100 wt % of the potassium formate present in the blend. The cesium sulfate can be added in an amount to react with from about 80 wt % to about 99.5 wt % or from about 95 wt % to 99 wt % of the potassium formate present in the blend. The cesium sulfate can be added as a single addition or can be added as multiple additions at separate times. The addition of the cesium sulfate can be continuous, semi-continuous, or batch-wise, or by single addition prior to the separating step. The amount of potassium formate present in the blend can be determined by standard measuring techniques, and/or can be determined based on the specific gravity of the overall blend or boiling point of the overall blend. For instance, FIG. 1 can be used to determine the wt % of the cesium formate and potassium formate based on a density measurement of the blend. As mention in some methods, rubidium sulfate can be used in addition to cesium sulfate or in lieu of cesium sulfate. The disclosure below and above regarding cesium sulfate and the steps that use the cesium sulfate can equally apply to methods that use or include rubidium sulfate.

For purposes of the present invention, the "adding" of cesium sulfate (and/or rubidium sulfate) can include or be or involve mixing, or dissolving, or blending, or dispersing, or combining the cesium sulfate (and/or rubidium sulfate) with the alkali metal formate blend using any conventional mixing or combining techniques including, but not limited to, a magnetic stirrer, an agitator, a mixer, a blender, and the like. Any conventional mixing, blending and/or combining techniques can be used including, but not limited to, magnetically induced stirring methods, pumping, in line circulation, inline static mixer, multi-styled traditional vertical and/or side-mount mechanical agitators, ribbon-like blenders, and the like. As long as the cesium sulfate (and/or rubidium sulfate) is introduced into the alkali metal blend such that the cesium sulfate (and/or rubidium sulfate) reacts with the potassium formate present in the alkali metal blend, the mixing or addition of the cesium sulfate (and/or rubidium sulfate) is sufficient for purposes of the present invention. For purposes of the present invention, the term "adding" includes adding cesium sulfate (and/or rubidium sulfate) to the blend, or adding the blend to the cesium sulfate (and/or rubidium sulfate), or co-additions.

The mixed alkali metal formate blend that is treated by any of the methods of the present invention can have a density or specific gravity of less than 2.4 s.g., such as less than 2.3 s.g., such as less than 2.2 s.g. Typically, the alkali metal formate blends that have cesium formate and potassium formate can generally have a density or specific gravity of from about 1.6 to about 2.2 s.g. To be clear, s.g. (specific gravity), which is dimensionless, is the ratio of the density (at 1 atm and 15.6° C.) of a substance to the density (mass of the same unit volume) of a reference substance, which here is water. The s.g. numbers provided in the present invention can alternatively be density in $g/cm^3$ for purposes of the present invention. The pH is measured by diluting the brine solution with water in a 10:1 (water solution) by volume. For instance, one can take 10 ml of brine solution and dilute with water to get 100 ml to test for pH.

With regard to the temperature that is used in the method to preferentially precipitate potassium sulfate, the temperature of the mixed alkali metal formate blend can be any temperature above freezing to the boiling temperature of the blend (e.g. about 110° C. to 150° C.), and is preferably at least 50° C. This temperature is the temperature of the alkali metal formate blend. The elevated temperature of at least 50° C., if used, can be achieved prior to the addition of the cesium sulfate (and/or rubidium sulfate), or it can be achieved during the addition of the cesium sulfate (and/or rubidium sulfate), or it can be achieved after addition of the cesium sulfate (and/or rubidium sulfate). This temperature of at least 50° C. can be from about 50° C. to the boiling point of the blend. The maintaining of this temperature for the alkali metal formate blend, once the cesium sulfate (and/or rubidium sulfate) is present and dissolved or dispersed or mixed in the alkali metal formate blend, is generally until the potassium sulfate precipitate is formed and, preferably, is held at this temperature (or increased further in temperature) until most or all of the potassium sulfate precipitate is formed or that is capable of forming due to solubility limits, which can be on the order of seconds to minutes.

As an option, the causing of the potassium sulfate precipitate to form can be done in one or more stages to more efficiently and more preferentially cause the formation of the potassium sulfate precipitate versus the formation of other precipitates, such as cesium sulfate precipitate. Preferably, the reaction is done in stages where the mixed alkali metal formate blend with the cesium sulfate (and/or rubidium sulfate) present is raised to a temperature of from about 50° C. to the boiling point of the blend to cause formation of just the potassium sulfate precipitate (a first stage). At this point, it is then preferred to lower the temperature to below 50° C. (e.g., remove the heat or cool the blend) and remove or separate the thus-formed potassium sulfate precipitate from the solution.

For any of the methods of the present application, the removal of the potassium sulfate precipitate can be done by any standard filtering or removal techniques, such as membranes, filter pads, filter paper, and the like. The removal of the potassium sulfate or precipitate can be executed by any appropriate liquid/solids separation techniques, or combinations thereof, such as pressure filtration, vacuum filtration, centrifugation, clarification, cyclone separation, screening by crystal sizing, settling the crystal phase and separating the aqueous phase by decanting, membrane, cartridge, and the like, while also using an appropriately specified media for the separation, as required.

For any of the methods of the present invention, the percentage (in wt %) of precipitate removed can be from about 1% to 100% of the precipitate present and preferably at least about 25%, at least about 50%, at least about 75%, at least about 85%, at least about 90%, at least about 95%, at least about 99% of the precipitate (based on the amount of precipitate present) can be removed.

The lowering of the temperature to below 50° C. can be done through any temperature reduction technique, such as an ice bath, water jacket, other cooling jackets, and the like. Then, the purified solution (with removed potassium sulfate precipitate) can be elevated to a temperature of from about 50° C. to the boiling temperature of this blend (that had precipitate removed) to remove water (e.g., reduce the water content) from this purified solution which causes the reduction in solubility of any remaining potassium sulfate to further occur (a second stage) and thus result in additional potassium sulfate precipitate. For instance, at this second stage of temperature elevation, the percent water in solution can be from about 16 wt % to about 36 wt %, and by boiling, can be reduced to from about 15 wt % to about 24 wt % water, based on the weight of the further purified solution. Then, after this formation of additional potassium sulfate precipitate, the further purified solution can be reduced in temperature to below 50° C., to again remove any additional precipitate formed, using the same removal or separating techniques as above.

Afterwards, the purified solution can optionally be subjected again to elevated temperatures, such as from about 50° C. to the boiling point of the further purified solution (a third stage), and preferably boiled again or subjected to temperatures to cause boiling and thus remove more water (e.g., reduce the water content further) from the further purified solution so that at least some remaining potassium sulfate if any, can fall out of solution and form a potassium sulfate precipitate. Again, by boiling to remove further water (e.g., reduce the water content further), the solubility of the potassium sulfate becomes more preferential to the potassium sulfate precipitate forming. At this point, for the removal of additional potassium sulfate precipitate, the percent water in solution can be from about 15 wt % to about 22 wt %.

Thus, with this process, the method can further comprise removing water from the purified solution (e.g., reducing the water content) in order to precipitate additional potassium sulfate and then involves separating at least a portion (or all) of the additional potassium sulfate precipitate from the purified solution, and these steps can be optionally repeated one or more times, such as two times, three times, four times, or five or more times in order to ensure that the potassium sulfate precipitate is removed to its desired or fullest extent.

While the mixed alkali metal blend can be raised to a temperature of at least 50° C. prior to, during, or after addition of the cesium sulfate (and/or rubidium sulfate), to maximize the amount of the potassium sulfate precipitate and minimize precipitates that contain cesium (and/or rubidium), it is preferred to have the mixed alkali metal formate blend at a temperature of about 50° C. or higher before addition of the cesium sulfate (and/or rubidium sulfate). In general, this optional elevation of temperature for the mixed alkali metal formate blend can be a temperature of from about 50° C. to the boiling point of the mixed alkali metal formate blend in solution. Depending on the particular blend, this temperature can be from about 110° C. to about 150° C., such as from about 110° C. to about 125° C., or from about 110° C. to about 115° C. The boiling point for this mixed alkali metal formate blend depends upon the amount of cesium formate present, the amount of potassium formate present, other formates present, other additives that may be present, and the amount of water present.

For purposes of the present invention, the addition of the cesium sulfate (and/or rubidium sulfate) to the mixed alkali metal formate blend can occur at temperatures below 50° C., such as from about 15° C. to about 50° C. and achieve the purposes of the present invention, which is to recover at least a portion of a particular alkali metal formate, such as cesium formate and/or rubidium formate. When using lower temperatures, such as below about 50° C., the ability of the potassium formate to react with the cesium sulfate (and/or rubidium sulfate) and preferentially precipitate potassium sulfate, decreases. Put another way, the more efficient process, so as to increase the amount of potassium sulfate precipitate and/or decrease or avoid formation of cesium sulfate precipitate (and/or rubidium sulfate precipitate), is to operate at temperatures of about 50° C. or higher. Temperatures that are higher are more preferred, meaning temperatures at or near the boiling point of the mixed alkali metal formate blend.

With regard to separating at least a portion (or all) of the sulfate precipitate from the solution to obtain a purified solution, this can be done at elevated temperatures or at a lower temperature, such as ambient temperatures, such as from about 15° C. to about 30° C. or from about 20° C. to about 30° C. If the mixed alkali metal formate blend is at an elevated temperature, then after the sulfate precipitate has formed, the mixed alkali metal formate blend can be reduced in temperature (e.g., cooled) or can remain at this elevated temperature for the separating step. Preferably, reducing the elevated temperature in a controlled fashion to a temperature below 50° C. is preferred. By having controlled cooling or a temperature profile, this permits an orderly crystallization of the salt from solution and, further, permits the crystallization to occur in the order of the metal salt's solubility. In other words, with orderly crystallization or an orderly reduction of temperature or step-wise reduction in temperature, this permits crystallization to occur in an orderly fashion such that the potassium sulfate precipitate crystallizes preferentially since its solubility is lower at each temperature compared to the cesium salt and/or rubidium salt. Thus, preferably, a rapid reduction in temperature is not preferred. For instance, a temperature reduction of 5° C. (or less) per minute can lead to orderly crystallization and a more orderly crystallization can occur at a temperature reduction of about 3° C. (or less) per minute, and an even more orderly crystallization can occur at a temperature reduction of about 1° C. (or less) per minute, and an even more orderly crystallization can occur at a temperature reduction of 0.5° C. (or less) per minute or a temperature reduction of 0.1° C. (or less) per minute. In other words, the slower the controlled cooling (or the slower the $\Delta T$ per minute), the more orderly the crystallization and the more preferential the potassium sulfate precipitates versus the precipitation of other salts, such as cesium and/or rubidium.

Thus, preferably, a temperature of about 50° C. or higher is used for purposes of reacting the cesium sulfate (and/or rubidium sulfate) with the mixed alkali metal formate blend, as this higher temperature makes the cesium salt (and/or rubidium salt) more soluble, whereas the potassium salt is not as soluble at this higher temperature, and, thus, this will lead to the preferential precipitation of the potassium sulfate. Then, by cooling in a controlled fashion, this keeps the potassium precipitate out of solution and drives out even more potassium precipitate as the temperature is controllably lowered so as to permit the orderly crystallization of the less soluble salts, namely potassium sulfates. Thus, an orderly decline of temperature preferentially permits more potassium sulfate to precipitate first, and this can continue with each controlled reduction in temperature. By using this preferred process, the preferential precipitation of potassium sulfate is achieved with less, to little, to none of the cesium precipitating (and/or rubidium precipitating) and, thus, remaining in solution for cesium formate (and/or rubidium formate) recovery.

With regard to the step of removing (e.g., reducing) water by heating or other techniques, as stated, removing water (e.g., reducing water content) alters the solubility of the salts present in solution. Thus, if the mixed alkali metal formate blend was raised to an elevated temperature at or near the boiling point of the mixed alkali metal formate blend for the precipitation reaction of cesium sulfate (and/or rubidium sulfate) with the alkali metal formate blend, this simultaneously removes some of the water. After the first separating of the potassium sulfate precipitate from the solution to obtain a purified solution, the removing of water from the purified solution can occur by re-heating the purified solution to near boiling or boiling. Typically, the temperature for this boiling point can actually be higher since the solubility changes due to a lower weight percent of water, and lower weight percent potassium formate in the blend.

It is optional and possible to remove additional potassium sulfate precipitate by raising the temperature to about 50° C. to the boiling point of the purified solution, and more effective results with regard to achieving additional potassium sulfate precipitate formation can occur at higher temperatures near or at the boiling point of the purified solution that contains any remaining potassium formate.

If the mixed alkali metal blend is subjected to elevated temperatures, such as 50° C. or higher (e.g., up to the boiling point of the mixed alkali metal blend), this temperature can be held for any length of time, but, in general, only a few seconds to minutes are needed for the potassium sulfate precipitate to preferentially form.

Optionally, for any of the methods of the present invention, besides the mixed alkali metal formates that are present in solution, which is generally water, because the mixed alkali metal formate blend is optionally a used product (e.g. oil field brine), oil/gas field additives may also be present in the solution. These oil/gas field additives can include, but are not limited to, starch, polymers, drill cuttings, oil, organics, inorganics, and the like. As just one example, the oil/gas additives can include primarily drill cuttings with or without components such as, but not limited to, clay, quartz, sand, calcium carbonate, gum (e.g., xantham), and/or starch (unmodified and/or modified, and/or optionally polymeric) and/or one or more polymers. As another example, the oil/gas additives can primarily include drilling cuttings and starch. As a further example, the oil/gas additives can primarily include drill cuttings and one or more polymers and/or other drilling fluid components (e.g., cellulose polymer(s), lubricant(s), corrosion inhibitor(s), biocide(s), scavenger(s)). The polymer(s) can be water soluble and/or water insoluble polymers. There can be three types of water soluble polymers: polysaccharides (e.g., biopolymers), modified polymers, and synthetic polymers (e.g., polyacrylamides). These non-formate ingredients, whether intentionally added or impurities from their use in hydrocarbon recovery efforts, can be removed prior to, during, and/or after the methods of the present invention have been used. Generally, these additives, such as oil/gas field additives, can amount to from about 0 wt % to about 15 wt % (e.g., 0.1 wt % to 10 wt %, 0.3 wt % to 8 wt %, 0.5 wt % to 4 wt %, 1 wt % to 5 wt %) based on the overall solution. If these additives are removed, one method to do so is to raise the pH of the solution to an even higher pH, such as to 11 to about 12.5 pH or higher. This can be done as a pre-treatment and/or a post-treatment and/or an intermediate treatment with respect to the methods of the present invention. For instance, as an option, a treatment using a hydroxide-containing compound or other base to raise the pH can be used. For instance, lime, potassium hydroxide, barium hydroxide, calcium hydroxide, strontium hydroxide, or soluble monovalent base(s) or soluble divalent base(s), can be added to the formate-containing solution. Generally, the amounts added are to raise the pH by a unit of one or two or three pH. For instance, the formate-containing solution can have a pH of from about 10 to 11 and sufficient hydroxide-containing compounds or other bases can be added to raise this pH by one, two, or three units, such as to 11 to about 13 pH. This can cause the oil field additives to precipitate and then can be removed by standard filtration techniques. When the optional treatment is used to remove oil field additives or similar types of additives and impurities, the use of a base to raise the pH can lead to the precipitation of these unwanted additives which could also lead to precipitation of calcium carbonate or barium carbonate or other precipitates depending upon which base is used. This optional treatment, to raise the pH and remove such oil/gas field additives or other impurities that can precipitate, can occur as a pre-treatment and/or as a post-treatment with respect to the processes of the present invention, and/or can occur as an intermediate treatment step in between the various process steps of the present invention.

With regard to the term "purified solution," for any of the methods of the present invention, this means that the amount of cesium formate and/or rubidium formate is increased by weight percent based on the overall weight of the solution compared to the starting mixed alkali metal formate blend that was subjected to the steps of the present invention. With the present invention, the amount of cesium formate (and/or rubidium formate) by weight percent, based on the overall weight percent of the mixed alkali metal formate blend in solution, is increased. With the present invention, the "purified solution," after one or more of the processes of the present invention, can achieve a cesium formate weight percent in solution of about 77 wt % to about 85 wt % cesium formate and/or rubidium formate in solution. With the present invention, the "purified solution," with regard to formate content, can contain from about 90 wt % to about 100 wt % cesium formate and/or rubidium formate, and all other formates that are not cesium formate or rubidium formate can be present in an amount of about 5 wt % or less (e.g., 5 wt % to 0 wt %, 5 wt % to 0.1 wt %, 4 wt % to 0.3 wt %, 3 wt % to 0.5 wt %), based on the total weight on an elemental bases of alkali metal (e.g., elemental Na, K, and Li) present in solution for the purified solution.

While intended to be illustrative, though, not intended to be representative of all instances, a "fully" restored, near saturated, buffered and sufficiently basic pH(d) cesium formate brine, that is considered stable at near room temperature, with a nominal SG≥2.20, can comprise elemental alkalis, respectively of about 35,000 ppm K or less (e.g., 1 ppm to 30,000 ppm K), about 15,000 ppm Na or less (e.g., 1 ppm to 10,000 ppm Na), and about 3,000 ppm Li or less (e.g., 1 ppm to 2,500 ppm Li). Water and rubidium formate can comprise the predominant balance of the brine. A formate brine of this sort can be recovered or restored by one or more methods of the present invention.

These "fully" restored nominal end-point values are presented as bases for quantifying the cited % purification values and ranges. However, it should be also recognized that the cesium formate fraction separated, recovered, and restored, from previously mixed formate oil-field brine blends, could be restored to lower specific gravities by the present methods and techniques, as well, to near saturation, as is desired or warranted.

These alkali values and the degree of purification from the mixed alkali formate brine that preceded it, can vary for purposes of the present invention.

If there are lower levels of lithium present, a disproportionately higher weight percentage of potassium and/or sodium can be retained within the restored cesium formate brines, and still remain stable at SG≥2.20. Similarly, if lower levels of sodium are present, disproportionately higher weight percentages of potassium, and/or a somewhat higher weight percentage of lithium can be tolerated and retained.

As a further example of the present invention, a method to recover or separate at least a portion of cesium formate and/or rubidium formate from a mixed alkali metal formate blend is described. The mixed alkali metal formate blend is in solution and contains at least one or more of Component 1) and one or more of Component 2). Component 1) can include cesium formate or rubidium formate or both. Component 2) can include potassium formate, lithium formate, or sodium formate, or any combination thereof. As in the above example, this method also involves adding cesium sulfate and/or rubidium sulfate to the mixed alkali metal formate blend. The mixed alkali metal formate blend prior to, during, or after the addition of the cesium sulfate and/or rubidium sulfate can be optionally at a temperature of at least 50° C. or raised to a temperature of at least 50° C. so as to preferentially form an alkali metal sulfate precipitate of Component 2) (potassium sulfate, lithium sulfate, and/or sodium sulfate precipitate) and form additional cesium formate or rubidium formate or both in the solution. The method then involves separating at least a portion of the alkali metal sulfate precipitate from the solution to obtain a purified solution.

FIG. 2 is a flow chart summarizing steps and optional steps that can be used when the process is used with cesium sulfate (and/or rubidium sulfate) addition. Specifically, a sequence of steps is shown for this one preferred process with optional steps being presented in dash lines. A starting mixed alkali metal formate blend in solution 10 is used and cesium sulfate (and/or rubidium sulfate) is added to this blend in the cesium sulfate addition (and/or rubidium sulfate addition) step 12. Optionally, the temperature of the blend from step 10 can be elevated in step 14 either before (step 14A), during (step 14B), or after (step 14C) of the sulfate addition step 12. Then, if an elevated temperature is used, this temperature can optionally be reduced to below 50° C. in step 16 using cooling jackets or other temperature reduction techniques. The precipitate, namely the potassium sulfate precipitate, can then be separated from solution in step 18 using standard separation techniques, such as filtering and the like. Then, in optional step 20, water can be removed (e.g., reduced) from this purified solution formed after step 18 by elevating the temperature, such as to a near boiling or boiling temperature for a period of time. If this step is used, then in step 22, the temperature can be reduced to below 50° C., and then in step 24, the further precipitate, namely potassium sulfate precipitate, can again be separated from this solution in step 24. Then, optionally, in step 26, further water can be removed (e.g., water content can be further reduced) by elevating the temperature of this purified solution from step 24 by elevating the temperature to preferably near a boiling or boiling point of this solution for a period of time. Then, after step 26, in step 28, the temperature can again be reduced to below 50° C. as an option using standard temperature reduction techniques, such as cooling jackets or plates. Then, after step 28, in step 30, this further precipitate, namely potassium sulfate precipitate that has formed during this optional step 26/28 can be removed in step 30 using the same removal techniques, such as filtration. Then, in step 34, the optional steps of 26 and 28 can optionally be repeated one or more times. Then, in step 32, a purified solution of cesium formate and/or rubidium formate is obtained. As indicated earlier, the removal of the precipitate can occur at any temperature, even at elevated temperatures, but it is more desirable and efficient to separate the precipitate from solution at a temperature of below 50° C.

Figure 3:
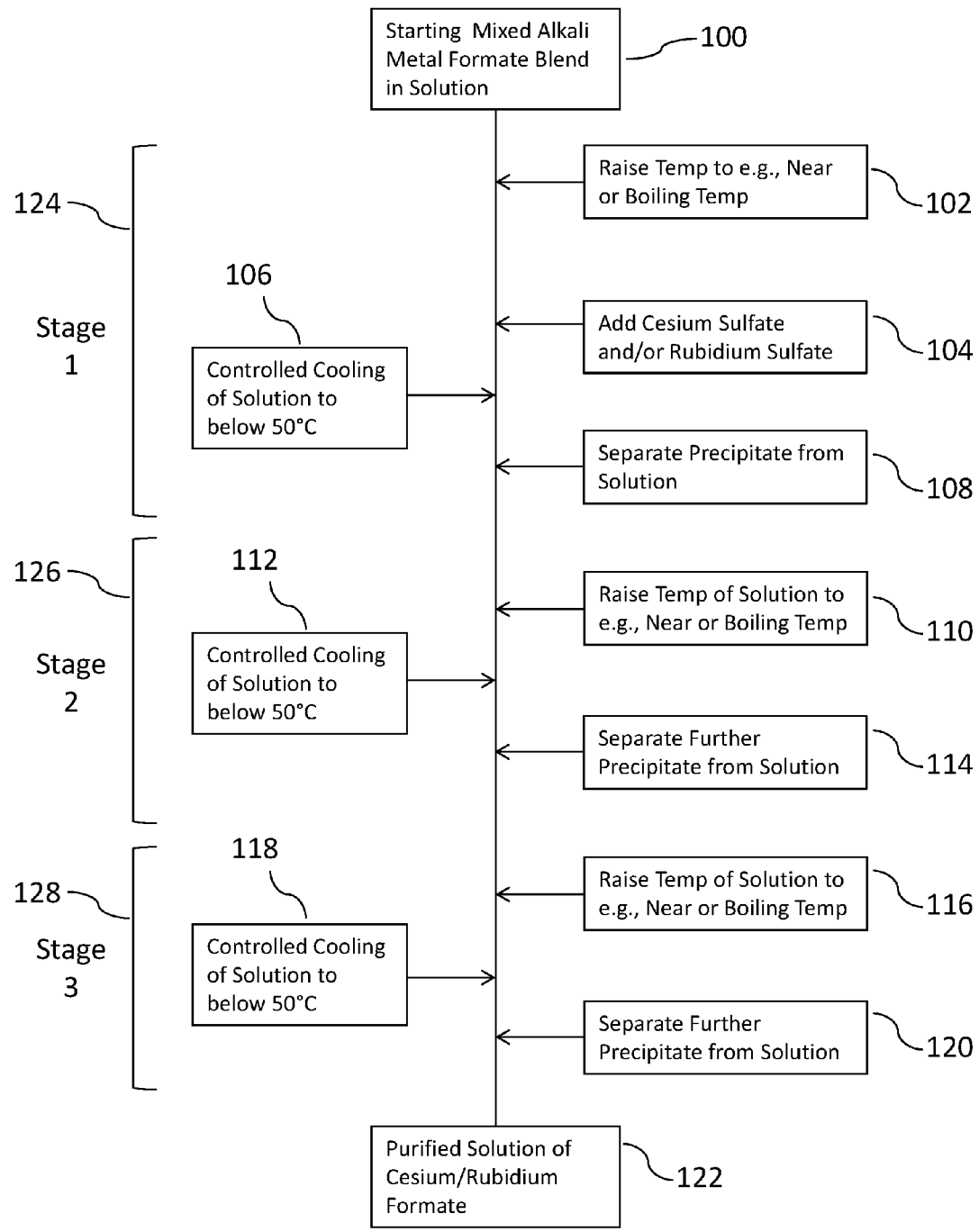

In FIG. 3, a preferred method using the cesium sulfate (and/or rubidium sulfate) addition is described. Further, the 3-stage process is identified and preferred in this method. In FIG. 3, a starting mixed alkali metal blend in solution is used and shown at step 100. Then, the temperature of this starting blend is raised to a near boiling or boiling temperature in step 102. Then, in step 104, cesium sulfate (and/or rubidium sulfate) is added to the blend at elevated temperature. Afterwards, in step 106, the controlled cooling of the solution to below 50° C. occurs in step 106, such as using a cooling jacket. Then, in step 108, the precipitate, namely the potassium sulfate precipitate (which can include, if present, lithium sulfate precipitate and sodium sulfate precipitate), is separated from the solution. Then, in step 110, the temperature of this solution from step 108 is elevated again to a near boiling or boiling temperature. Then, in step 112, the controlled cooling of this solution occurs, where the controlled cooling brings the solution down to a temperature below 50° C. In step 114, the further precipitate that has formed is then separated from solution. Then, in step 116, the temperature of this solution resulting from step 114 is then elevated again to a near boiling or boiling temperature of the solution. Then, in step 118, controlled cooling of this solution occurs to a temperature of below 50° C. Then, in step 120, any further precipitate that is formed is again separated from this solution to result in a purified solution of cesium formate and/or rubidium formate in step 122. In FIG. 3, stage 1 (124), stage 2 (126), and stage 3 (128) are shown.

In yet another example, the present invention relates to a method to recover or separate at least a portion of cesium formate (and/or rubidium formate) from a mixed alkali metal formate blend. The mixed alkali metal formate blend is in solution. The method includes adding cesium carbonate or cesium bicarbonate or both (and/or rubidium carbonate or rubidium bicarbonate or both) to the mixed alkali metal formate blend. The mixed alkali metal formate blend prior to, during, or after the addition of cesium carbonate and/or cesium bicarbonate can optionally be at a temperature of at least 50° C. or raised to a temperature of at least 50° C. so as to preferentially precipitate potassium carbonate and/or potassium bicarbonate precipitate, as well as form additional cesium formate (and/or rubidium formate) in solution. The method then involves separating at least a portion of the potassium carbonate precipitate and/or potassium bicarbonate precipitate from the solution to obtain a purified solution.

In a further similar example, the present invention relates to a method to recover or separate at least a portion of cesium formate or rubidium formate or both from a mixed alkali metal formate blend in solution. The mixed alkali metal formate blend in solution comprises at least one Component 1) and at least one Component 2). Component 1) can include cesium formate or rubidium formate or both. Component 2) can include potassium formate, lithium formate, or sodium formate, or any combination thereof. In this method, cesium carbonate and/or cesium bicarbonate and/or rubidium carbonate and/or rubidium bicarbonate is added to the mixed alkali metal formate blend. One or more of Component 2) reacts with the cesium carbonate and/or cesium bicarbonate and/or rubidium carbonate and/or rubidium bicarbonate and forms an alkali metal carbonate precipitate or an alkali metal bicarbonate precipitate or both. This reaction additionally forms cesium formate and/or rubidium formate in the solution. The method then involves separating at least a portion of the alkali metal carbonate and/or alkali metal bicarbonate precipitate from the solution to obtain a purified solution.

With regard to the cesium carbonate, this is commercially available from Cabot Corporation, and can be in powder form or in solution. When in solution, the cesium carbonate can typically be a 50 wt % to 70 wt % solution of cesium carbonate in solution. Preferably, though optional, the cesium carbonate and/or cesium bicarbonate is of high purity, such as about 90 wt % or higher, or 95 wt % or higher (e.g., 95% to 99.999%) pure cesium carbonate and/or cesium bicarbonate. When in solution at 15 to 30° C., rubidium carbonate can typically be a 50 wt % to 70 wt % solution of rubidium carbonate in solution. Preferably, though optional, the rubidium carbonate and/or rubidium bicarbonate is of high purity, such as about 90 wt % or higher, or 95 wt % or higher (e.g., 95% to 99.999%) pure rubidium carbonate and/or rubidium bicarbonate. The rubidium carbonate and/or bicarbonate can be obtained to order from Chemetall GmbH. Rubidium carbonate or bicarbonate can be formed by bubbling $CO_2$ into cesium and/or rubidium hydroxide and continue addition of $CO_2$ until the pH goes down to 11.2 (to form carbonate) or to about 8.1 (to form bicarbonate). The cesium carbonate and/or cesium bicarbonate and/or rubidium carbonate and/or rubidium bicarbonate can be added in any form, such as a powder or liquid. The amount of cesium carbonate and/or cesium bicarbonate and/or rubidium carbonate and/or rubidium bicarbonate added to the mixed alkali metal formate blend is dependent upon the amount of potassium formate present in the mixed alkali metal formate blend. Generally, the amount of the cesium carbonate and/or cesium bicarbonate and/or rubidium carbonate and/or rubidium bicarbonate added is an amount that reacts with most or all of the potassium that is from the potassium formate so as to form a potassium carbonate and/or potassium bicarbonate, and preferably without any excess cesium carbonate and/or cesium bicarbonate and/or rubidium carbonate and/or rubidium bicarbonate remaining or an amount below 5 wt % or below 1 wt % cesium carbonate and/or cesium bicarbonate and/or rubidium carbonate and/or rubidium bicarbonate based on the weight of solution. Thus, ideally, the amount of cesium carbonate and/or cesium bicarbonate and/or rubidium carbonate and/or rubidium bicarbonate introduced is preferably only an amount that reacts with the potassium formate and preferably is used up in the reaction that forms the potassium carbonate precipitate and/or potassium bicarbonate precipitate. For instance, the cesium carbonate and/or cesium bicarbonate and/or rubidium carbonate and/or rubidium bicarbonate can be added in an amount to react with from about 10 wt % to about 100 wt % of the potassium formate present in the blend. The cesium carbonate and/or cesium bicarbonate and/or rubidium carbonate and/or rubidium bicarbonate can be added in an amount to react with from about 80 wt % to about 99.5 wt % or from about 90 wt % to 95 wt % of the potassium formate present in the blend. The cesium carbonate and/or cesium bicarbonate and/or rubidium carbonate and/or rubidium bicarbonate can be added as a single addition or can be added as multiple additions at separate times. The addition of the cesium carbonate and/or cesium bicarbonate and/or rubidium carbonate and/or rubidium bicarbonate can be continuous, semi-continuous, or batch-wise, or by single addition prior to the separating step. The amount of potassium formate present in the blend can be determined by standard measuring techniques, and/or can be determined based on the specific gravity of the overall blend or boiling point of the overall blend. As an example, FIG. 1 can be used to determine the wt % of the cesium formate and potassium formate based on a density measurement of a nearly saturated blend.

For purposes of the present invention, the "adding" of cesium carbonate and/or cesium bicarbonate and/or rubidium carbonate and/or rubidium bicarbonate can include or be or involve mixing, or dissolving, or blending, or dispersing, or combining the cesium carbonate and/or cesium bicarbonate and/or rubidium carbonate and/or rubidium bicarbonate with the alkali metal formate blend using any conventional mixing or combining techniques including, but not limited to, a magnetic stirrer, an agitator, a mixer, a blender, and the like. Any conventional mixing, blending and/or combining techniques can be used including, but not limited to, magnetically induced stirring methods, pumping, in line circulation, inline static mixer, multi-styled traditional vertical and/or side-mount mechanical agitators, ribbon-like blenders, and the like. As long as the cesium carbonate and/or cesium bicarbonate and/or rubidium carbonate and/or rubidium bicarbonate is introduced into the alkali metal blend such that the cesium carbonate and/or cesium bicarbonate and/or rubidium carbonate and/or rubidium bicarbonate reacts with the potassium formate present in the alkali metal blend, the mixing or addition of the cesium carbonate and/or cesium bicarbonate and/or rubidium carbonate and/or rubidium bicarbonate is sufficient for purposes of the present invention. For purposes of the present invention, the term "adding" includes adding cesium carbonate and/or cesium bicarbonate and/or rubidium carbonate and/or rubidium bicarbonate to the blend, or adding the blend to the cesium carbonate and/or cesium bicarbonate and/or rubidium carbonate and/or rubidium bicarbonate.

As with the other methods, as an option, the alkali metal formate blend can be at a temperature or raised to a temperature of about 50° C. or higher, such as from about 50° C. to the boiling point or near boiling point of the alkali metal formate blend. As indicated above, higher temperatures permit a more preferential precipitation reaction of Component 2) with the cesium carbonate and/or cesium bicarbonate and/or rubidium carbonate and/or rubidium bicarbonate, depending upon which is added, to form an alkali metal carbonate or alkali metal bicarbonate precipitate and additional cesium formate, rubidium formate, or both in the solution.

In this method, as with the other methods, it is preferred to raise the temperature of the alkali metal formate blend prior to the addition of the cesium carbonate and/or cesium bicarbonate and/or rubidium carbonate and/or rubidium bicarbonate.

With regard to the temperature that is used in the method to preferentially precipitate potassium carbonate/potassium bicarbonate precipitate, the temperature of the mixed alkali metal formate blend can be any temperature above freezing to the boiling temperature of the blend, and is preferably at least 50° C. This temperature is the temperature of the alkali metal formate blend. The elevated temperature of at least 50° C., if used, can be achieved prior to the addition of the cesium carbonate and/or cesium bicarbonate and/or rubidium carbonate and/or rubidium bicarbonate, or it can be achieved during the addition of the cesium carbonate and/or cesium bicarbonate and/or rubidium carbonate and/or rubidium bicarbonate, or it can be achieved after addition of the cesium carbonate and/or cesium bicarbonate and/or rubidium carbonate and/or rubidium bicarbonate. This temperature of at least 50° C. can be from about 50° C. to the boiling point of the blend. The maintaining of this temperature for the alkali metal formate blend, once the cesium carbonate and/or cesium bicarbonate and/or rubidium carbonate and/or rubidium bicarbonate is present and dissolved or dispersed or mixed in the alkali metal formate blend, is generally until the potassium carbonate precipitate and/or potassium bicarbonate precipitate is formed or occurs and, preferably, is at this temperature or above until most or all of the potassium carbonate and/or potassium bicarbonate precipitate is formed or that is capable of forming due to solubility limits (e.g. at 15 to 30° C.), which can be on the order of seconds to minutes.

As an option, the causing of the potassium carbonate and/or potassium bicarbonate precipitate to form can be done in one or more stages to more efficiently and preferentially cause the formation of the potassium precipitate versus the formation of other precipitates, such as cesium carbonate and/or cesium bicarbonate precipitate and/or rubidium carbonate and/or rubidium bicarbonate precipitate. For instance, the reaction can be done in stages where the mixed alkali metal formate blend with the cesium carbonate and/or cesium bicarbonate and/or rubidium carbonate and/or rubidium bicarbonate present can be raised to a temperature of from about 50° C. to the boiling point of the blend to cause formation of just the potassium carbonate and/or potassium bicarbonate precipitate (a first stage). At this point, the temperature can be reduced to below 50° C. (e.g., cool the blend) to remove or separate the thus-formed potassium carbonate and/or potassium bicarbonate precipitate from the solution.

The lowering of the temperature to below 50° C. can be done through any temperature reduction technique, such as an ice bath, water jacket, other cooling jackets, and the like. Then, the purified solution (with removed potassium carbonate and/or potassium bicarbonate precipitate) can be elevated to a temperature of from about 50° C. to the boiling temperature of this blend (that had precipitate removed) to remove water or additional water (e.g., reduce water content) from this purified solution which causes the reduction in solubility (lower solubility) of any remaining potassium carbonate and/or potassium bicarbonate to further occur (a second stage) and thus result in additional potassium carbonate and/or potassium bicarbonate precipitate. For instance, at this second stage of temperature elevation, the percent water in solution can be from about 16 wt % to about 36 wt %, and by boiling, can be reduced to from about 15 wt % to about 24 wt % water, based on the weight of the further purified solution. Then, after this formation of additional potassium carbonate and/or potassium bicarbonate precipitate, the potassium carbonate and/or potassium bicarbonate precipitate can be reduced in temperature to below 50° C., to again remove the precipitate using the same removal or separating techniques as above.

Afterwards, the purified solution can optionally be subjected again to elevated temperatures, such as from about 50° C. to the boiling point of the further purified solution (a third stage), and preferably boiled again or subjected to temperatures to cause boiling and thus remove more water (e.g., further reduce water content) from the further purified solution so as to ensure that any remaining potassium carbonate and/or potassium bicarbonate can fall out of solution and form a potassium carbonate and/or potassium bicarbonate precipitate. Again, by boiling to remove further water, the solubility of the potassium carbonate and/or potassium bicarbonate becomes more conducive to the potassium carbonate and/or potassium bicarbonate precipitate forming. At this point, for the removal of additional potassium carbonate and/or potassium bicarbonate precipitate, the percent water in solution can be from about 15 wt % to about 22 wt %.

Thus, with this process, the method can further comprise removing water from the purified solution in order to precipitate additional potassium carbonate and/or potassium bicarbonate and then involves separating at least a portion of the additional potassium carbonate and/or potassium bicarbonate precipitate from the purified solution, and these steps can be optionally repeated one or more times, such as two times, three times, four times, or five or more times in order to ensure that the potassium carbonate and/or potassium bicarbonate precipitate is removed to its desired or fullest extent.

While the mixed alkali metal blend can be raised to a temperature of at least 50° C. prior to, during, or after addition of the cesium carbonate and/or cesium bicarbonate and/or rubidium carbonate and/or rubidium bicarbonate, to maximize the amount of the potassium carbonate and/or potassium bicarbonate precipitate and minimize precipitates that contain cesium and/or rubidium, it is preferred to have the mixed alkali metal formate blend at a temperature of about 50° C. or higher before addition of the cesium carbonate and/or cesium bicarbonate and/or rubidium carbonate and/or rubidium bicarbonate. In general, this optional elevation of temperature for the mixed alkali metal formate blend can be a temperature of from about 50° C. to the boiling point of the mixed alkali metal formate blend in solution. Depending on the particular blend, this temperature can be from about 110° C. to about 150° C., such as from about 110° C. to about 125° C., or from about 110° C. to about 115° C. The boiling point for this mixed alkali metal formate blend depends upon the amount of cesium formate and/or rubidium formate present, the amount of potassium formate present, other additives that may be present, and the amount of water present.

For purposes of the present invention, the addition of the cesium carbonate and/or cesium bicarbonate and/or rubidium carbonate and/or rubidium bicarbonate to the mixed alkali metal formate blend can occur at temperatures below 50° C., such as from about 15° C. to about 50° C. and achieve the purposes of the present invention, which is to recover at least a portion of a particular alkali metal formate, such as cesium formate and/or rubidium formate. When using lower temperatures, such as below about 50° C., the ability of the potassium formate to react with the cesium carbonate and/or cesium bicarbonate and/or rubidium carbonate and/or rubidium bicarbonate and preferentially precipitate potassium carbonate and/or potassium bicarbonate decreases. Put another way, the more efficient process, so as to increase the amount of potassium carbonate and/or potassium bicarbonate precipitate and/or decrease or avoid any cesium carbonate and/or cesium bicarbonate precipitate, is to operate at temperatures of about 50° C. or higher. Temperatures that are higher are more preferred, meaning temperatures at or near the boiling point of the mixed alkali metal formate blend.

With regard to separating at least a portion of the carbonate and/or bicarbonate precipitate from the solution to obtain a purified solution, this can be done at elevated temperatures or at a lower temperature, such as ambient temperatures, such as from about 20° C. to about 25° C. If the mixed alkali metal formate blend is at an elevated temperature, then after the potassium carbonate and/or potassium bicarbonate precipitate has formed, the mixed alkali metal formate blend can be reduced in temperature (e.g., cooled) or can remain at this elevated temperature for the separating step. Preferably, reducing the elevated temperature in a controlled fashion to a temperature below 50° C. is preferred. By having controlled cooling or a temperature profile, this permits an orderly crystallization of the salt from solution and, further, permits the crystallization to occur in the order of the metal salt's solubility. In other words, with orderly crystallization or an orderly reduction of temperature or step-wise reduction in temperature, this permits crystallization to occur in an orderly fashion such that the potassium carbonate and/or potassium bicarbonate precipitate crystallizes preferentially since its solubility is lower at each temperature compared to the cesium salt and/or rubidium salt. Thus, preferably, a rapid reduction in temperature is not preferred. For instance, a temperature reduction of 5° C. (or less) per minute can lead to orderly crystallization and a more orderly crystallization can occur at a temperature reduction of about 3° C. (or less) per minute, and an even more orderly crystallization can occur at a temperature reduction of about 1° C. (or less) per minute, and an even more orderly crystallization can occur at a temperature reduction of 0.5° C. (or less) per minute or a temperature reduction of 0.1° C. (or less) per minute. In other words, the slower the controlled cooling (or the slower the $\Delta T$ per minute), the more orderly the crystallization and the more preferential the potassium carbonate and/or potassium bicarbonate precipitates versus the precipitation of other salts, such as cesium and/or rubidium.

Thus, preferably, a temperature of about 50° C. or higher is used for purposes of reacting the cesium carbonate and/or cesium bicarbonate and/or rubidium carbonate and/or rubidium bicarbonate with the mixed alkali metal formate blend, as this higher temperature makes the cesium salt (and/or rubidium salt) more soluble, whereas the potassium salt is not as soluble at this higher temperature, and, thus, this will lead to the preferential precipitation of the potassium carbonate and/or potassium bicarbonate. Then, by cooling in a controlled fashion, this keeps the potassium precipitate out of solution and drives out even more potassium precipitate as the temperature is controllably lowered so as to permit the orderly crystallization of the less soluble salts, namely potassium carbonate and/or potassium bicarbonates. Thus, an orderly decline of temperature preferentially permits more potassium carbonate and/or potassium bicarbonate to precipitate first, and this can continue with each controlled reduction in temperature. By using this preferred process, the preferential precipitation of potassium carbonate and/or potassium bicarbonate precipitate is achieved with less, or little to none of the cesium (and/or rubidium) precipitating and, thus, remaining in solution for cesium formate (and/or rubidium formate) recovery.

With regard to the step of removing (e.g., reducing) water by heating or other techniques, as stated, removing (e.g., reducing water content) water alters the solubility of the salts present in solution. Thus, if the mixed alkali metal formate blend was raised to an elevated temperature at or near the boiling point of the mixed alkali metal formate blend for the precipitation reaction of cesium carbonate and/or cesium bicarbonate and/or rubidium carbonate and/or rubidium bicarbonate with the alkali metal formate blend, this simultaneously removes some of the water. After the first separating of the potassium carbonate and/or potassium bicarbonate precipitate from the solution to obtain a purified solution, the removing of water (e.g., reducing of water content) from the purified solution can occur by re-heating the purified solution to near boiling or boiling. Typically, the temperature for this boiling point can actually be higher since the solubility changes due to a lower weight percent of water, and lower weight percent potassium formate in the blend.

It is optional and possible to remove any additional potassium carbonate and/or potassium bicarbonate precipitate by raising the temperature to about 50° C. to the boiling point of the purified solution, but more effective results with regard to achieving additional potassium carbonate and/or potassium bicarbonate precipitate formation can occur at higher temperatures near or at the boiling point of the purified solution that contains any remaining potassium formate.

If the mixed alkali metal blend is subjected to elevated temperatures, such as 50° C. or higher (e.g., to the boiling point of the mixed alkali metal blend), this temperature can be held for any length of time, but, in general, only a few seconds to minutes are needed for the potassium carbonate and/or potassium bicarbonate precipitate to preferentially form.

With the methods involving the cesium carbonate/cesium bicarbonate addition and/or rubidium carbonate/rubidium bicarbonate addition, multiple stages of removing precipitate and then, optionally, re-heating are not as beneficial as with the cesium sulfate (and/or rubidium sulfate) addition methods. Because cesium carbonate and/or cesium bicarbonate and/or rubidium carbonate and/or rubidium bicarbonate have a different solubility than the cesium sulfate, it has been discovered that, in general, the entire (or large amount) alkali metal carbonate precipitate and/or alkali metal bicarbonate precipitate can come out of solution in one stage, though multiple stages can be used.

Thus, as an option, as with the other methods, the methods involving the cesium carbonate/cesium bicarbonate and/or rubidium carbonate/rubidium bicarbonate can optionally include removing water (e.g., reducing water content) from the purified solution in order to precipitate any additional alkali metal carbonate precipitate or alkali metal bicarbonate precipitate, and can further optionally involve separating at least a portion of this additional alkali metal carbonate precipitate or alkali metal bicarbonate precipitate from the purified solution, and these steps can be optionally repeated one or more times. The removing of the water (e.g., reducing of water content) can be achieved in the same manner as described for the other methods, namely, by heating to near or at the boiling point of the purified solution.

As an additional option, with the methods involving the cesium carbonate/cesium bicarbonate additions and/or rubidium carbonate/rubidium bicarbonate additions, the recovered alkali metal carbonate precipitate and/or alkali metal bicarbonate precipitate can then be further treated by adding water and formic acid to this precipitate, which will lead to the formation of an alkali metal formate for further use. For instance, if the alkali metal carbonate or alkali metal bicarbonate precipitate was potassium carbonate precipitate or potassium bicarbonate precipitate, adding water and formic acid would lead to the formation of a useful potassium formate in solution. The amount of water and formic acid added to the alkali metal carbonate/alkali metal bicarbonate precipitate is an amount sufficient to form generally an alkali metal formate in solution and, thus, the amount of formic acid and water can be added as a single batch, or incrementally, in order to have the formate stay in solution.

Figure 4:
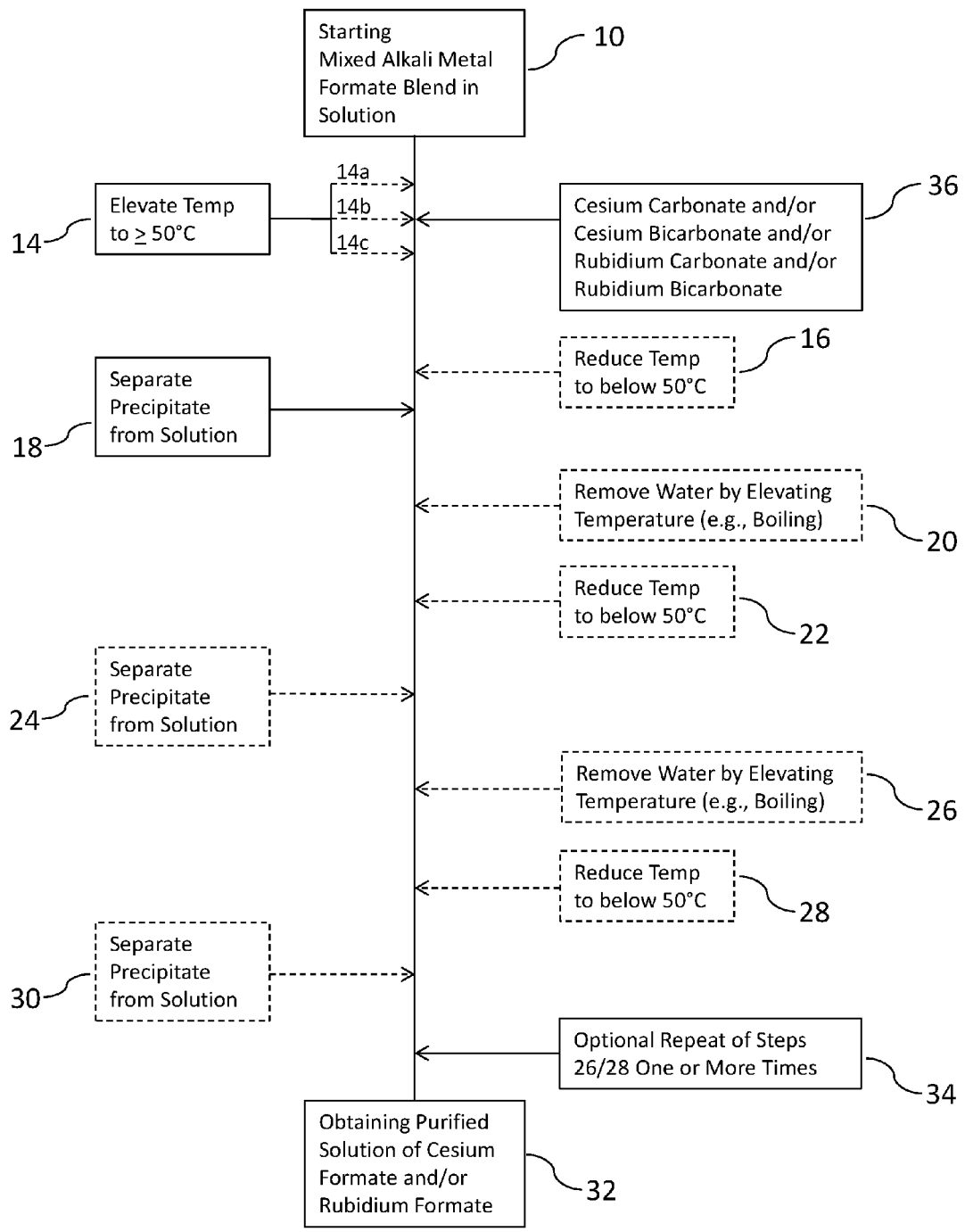

In FIG. 4, the steps identified are the same as in FIG. 2, except step 12 is replaced with step 36, which shows the addition of cesium carbonate and/or cesium bicarbonate (and/or rubidium carbonate and/or rubidium bicarbonate). Otherwise, the steps as described in FIG. 2 apply equally to the steps shown in FIG. 4.

Figure 5:
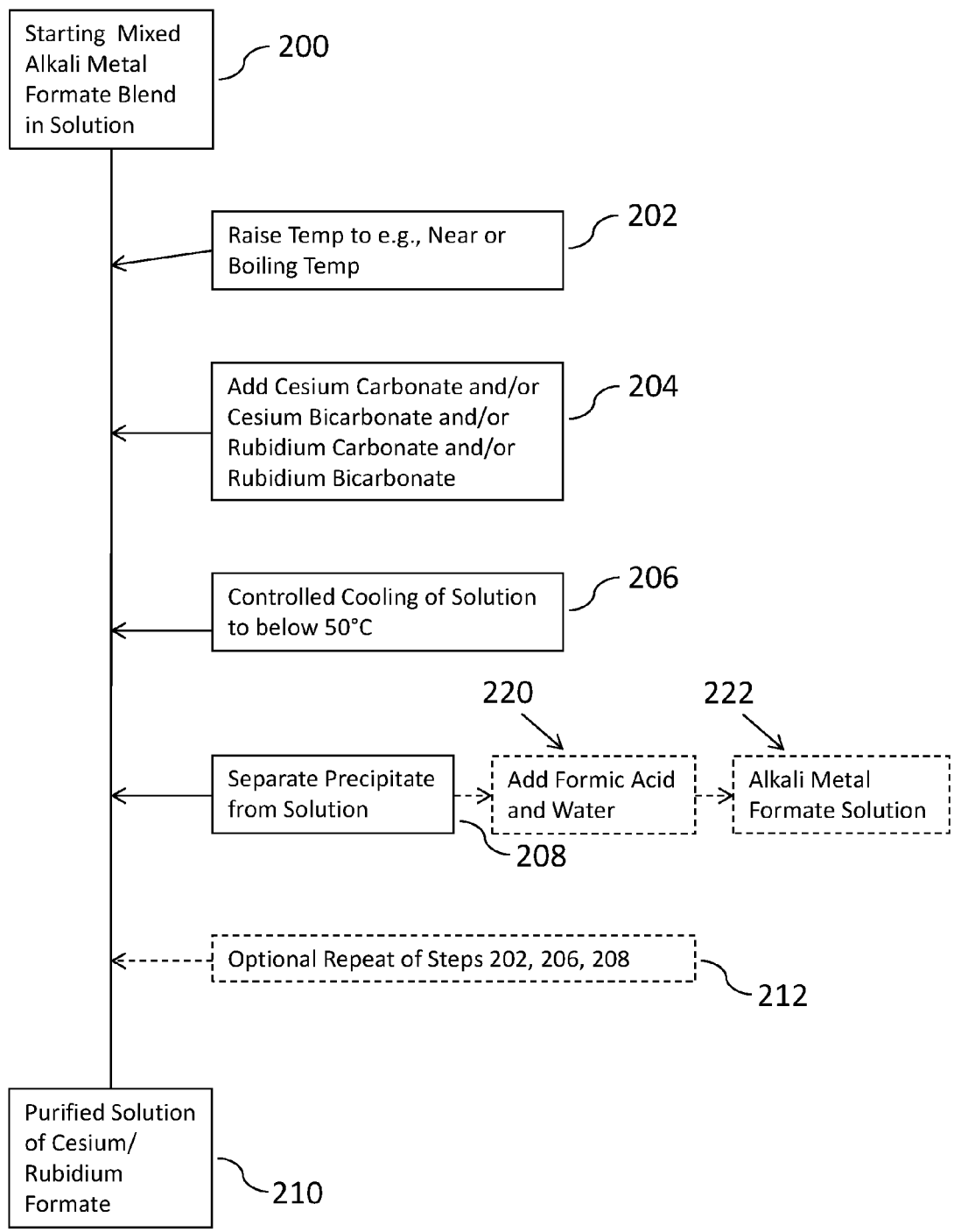

Then, in FIG. 5, a preferred process using the cesium carbonate and/or cesium bicarbonate (and/or rubidium carbonate and/or rubidium bicarbonate) is described. In this process, a starting mixed alkali formate blend in solution is used as represented by step 200. In step 202, the temperature of this mixed alkali formate blend in solution is raised to a temperature, for instance, of a near boiling or boiling temperature. Then, in step 204, cesium carbonate and/or cesium bicarbonate and/or rubidium carbonate and/or rubidium bicarbonate are added to the blend at elevated temperature. Then, in step 206, a controlled cooling of this solution to below 50° C. is done. Then, in step 208, the precipitate that is formed, which is potassium carbonate and/or potassium bicarbonate (and, optionally, sodium carbonate and/or sodium bicarbonate and, optionally, lithium carbonate and/or lithium bicarbonate, if present) occurs. The steps of 202, 206, and 208 can be optionally repeated one or more times as shown in step 212. Then, in step 210, the purified solution of cesium formate and/or rubidium formate is obtained.

Further, in FIG. 5, as an option, after step 208, where the precipitate is separated from the solution, this precipitate can optionally be added with formic acid and water in step 220, which will lead to the formation of an alkali metal formate solution in step 222, such as potassium formate or other formates that were part of the precipitate. This reaction can occur at room temperature, for instance, at 20° C. to 30° C., or other temperatures, such as elevated temperatures. These optional steps can also be used in the process shown in FIG. 4.

For purposes of all methods of the present invention, the term "preferentially precipitates" with respect to forming a particular type or form of precipitate, is intended to be where one precipitation reaction occurs predominately or occurs more so than other precipitation reactions with regards to weight percent of precipitate formed. In other words, one salt (precipitate) falls out of solutions more so than other salts. For instance, and only as an example, when the cesium sulfate reacts with the potassium formate and preferentially precipitates potassium sulfate, this means that more (by wt %) potassium sulfate precipitate will form and fall out of solution versus other alkali metal sulfate precipitates like cesium sulfate precipitate. As another example, and only as an example, when the cesium carbonate and/or cesium bicarbonate reacts with the potassium formate and preferentially precipitates potassium carbonate and/or potassium bicarbonate, this means that more (by wt %) potassium carbonate and/or potassium bicarbonate precipitate will form versus other alkali metal carbonate/bicarbonate precipitates like cesium carbonate/cesium bicarbonate precipitate. Preferably, the term "preferentially" can include the situation where the intended precipitate (e.g., potassium sulfate, potassium carbonate, potassium bicarbonate, or other non-cesium and/or non-rubidium containing precipitates) forms at least 50 wt %, at least 75 wt %, at least 80 wt %, at least 85 wt %, at least 90 wt %, at least 95 wt %, at least 97 wt %, at least 99 wt % or from about 50 wt % to about 100 wt % of the total weight percent precipitate formed in the reaction that forms the precipitate.

With any of the above methods of the present invention, the methods of separating the cesium formate and/or rubidium formate can be done in the absence of any barium compound, such as barium hydroxide.

In any of the above methods of the present invention, the purified solution, after one or more separating techniques, can have a specific gravity of from about 2 to about 2.3 s.g. at 25° C., such as 2 to about 2.3 s.g at 25° C. or from about 2.2 to about 2.3 s.g. at 25° C.

In any of the above methods of the present invention (above or below), the purified solution, after one or more separating steps, can have a sulfate level of 16,000 ppm or less, 8,000 ppm or less, 5,000 ppm or less, 2,400 ppm or less, 1,200 ppm or less, 600 ppm or less, 100 ppm or less, or from about 1 ppm to 5,000 ppm, or from about 50 ppm to 5,000 ppm, or from about 75 ppm to 8,000 ppm, all with respect to the purified solution that contains the cesium formate and/or rubidium formate. Needless to say, for the carbonate/bicarbonate process, the sulfate levels are zero or close to zero (less than 100 ppm).

The present invention also relates to methods to form cesium hydroxide from cesium sulfate. Preferably the method forms a cesium hydroxide in solution from a cesium sulfate in solution. Thus, the starting solution comprises, consists of, includes, or contains at least cesium sulfate in solution. The resulting solution or end product comprises, consists of, includes, or contains at least cesium hydroxide in solution.

By using this method(s), a cesium hydroxide solution of high purity or higher purity can be obtained (e.g., the solution contains water and cesium hydroxide), wherein the water and cesium hydroxide comprise over 75 wt %, over 85 wt %, over 95 wt %, or 75 wt % to 100 wt %, or 85 wt % to 99 wt %, or 95 wt % to 99.9 wt % of the resulting solution, based on the total weight of the resulting solution.

With regard to the cesium sulfate solution that is treated by this method of the present invention, the cesium sulfate-containing solution is or can be partly or nearly or fully saturated with regard to the cesium sulfate salt. A nearly or fully saturated cesium sulfate solution that can typically range from about 35 wt % to about 50 wt % water based on the overall weight of the cesium sulfate-containing solution.

As just one example of the present invention, a method to at least partially or fully covert the cesium sulfate in solution to cesium hydroxide is described. However to be clear, this method (as described above and below) can be used in the same manner to convert a rubidium sulfate in solution to rubidium hydroxide, or can be used to convert a cesium sulfate/rubidium sulfate in solution to cesium hydroxide/rubidium hydroxide.

The method includes adding potassium hydroxide to the starting solution (namely, the cesium sulfate solution) to form cesium hydroxide in solution and to form potassium sulfate precipitate (as a solid). The cesium sulfate reacts with the potassium hydroxide to form the cesium hydroxide and to form the potassium sulfate precipitate. As an option, the cesium sulfate solution prior to, during, or after the addition of the potassium hydroxide can be at a temperature of at least 50° C. or raised to a temperature of at least 50° C. so as to preferentially precipitate potassium sulfate, as well as form cesium hydroxide in solution. The method then involves separating at least a portion of the potassium sulfate precipitate from the solution to obtain a resulting solution of cesium hydroxide or a solution containing cesium hydroxide.

In more detail, for this method of the present invention, the starting cesium sulfate in solution can contain from about 1 wt % to about 100 wt % cesium sulfate based on the weight of the alkali metal salts present in solution. For example, the starting solution can contain from about 20 wt % to about 99 wt % cesium sulfate, from about 40 wt % to about 95 wt % cesium sulfate, or from about 75 wt % to about 99 wt % cesium sulfate, or from about 85 wt % to about 99.9 wt % percent cesium sulfate, based on the weight of the alkali metal salts present in the solution.

With regard to adding the potassium hydroxide to the cesium sulfate in solution, the potassium hydroxide can be any commercially-available grade of potassium hydroxide. The potassium hydroxide is commercially available, and can be used in powder form or in solution form. When in solution form, for instance, the solution can be a 45 wt % to 50 wt % potassium hydroxide solution. Anhydrous potassium hydroxide (e.g., 90 wt % KOH) can be used. Preferably, though optional, the potassium hydroxide is of high purity, such as about 90 wt % or higher, or 95 wt % or higher (e.g., 95% to 99.999%) pure potassium hydroxide. The potassium hydroxide can be added in any form, such as a powder or liquid. The amount of potassium hydroxide added to the starting solution is dependent upon the amount of cesium sulfate present in solution. Generally, the amount of the potassium hydroxide added is an amount that reacts with most or all of the cesium that is from the cesium sulfate so as to form a potassium sulfate precipitate, and preferably without any excess potassium hydroxide remaining or an amount below 5 wt % (e.g. below 3 wt %, below 1 wt % such as 0 wt % to 4.9 wt %) potassium hydroxide based on the weight of solution. Thus, ideally, the amount of potassium hydroxide introduced is preferably only an amount that reacts with the cesium sulfate and preferably is used up in the reaction that forms the potassium sulfate precipitate. For instance, the potassium hydroxide can be added in an amount to react with from about 10 wt % to about 100 wt % of the cesium sulfate present in the starting solution. The potassium hydroxide can be added in an amount to react with from about 80 wt % to about 99.5 wt % or from about 95 wt % to 99 wt % of the cesium sulfate present in the solution. The potassium hydroxide can be added as a single addition or can be added as multiple additions at separate times. The addition of the potassium hydroxide can be continuous, semi-continuous, or batch-wise, or by single addition prior to the separating step. The amount of cesium sulfate present in the blend can be determined by standard measuring techniques, and/or can be determined based on the specific gravity of the overall blend or boiling point of the overall blend.

For purposes of the present invention, the "adding" of potassium hydroxide can include or be or involve mixing, or dissolving, or blending, or dispersing, or combining the potassium hydroxide with the starting solution that contains the cesium sulfate (and/or rubidium sulfate) using any conventional mixing or combining techniques including, but not limited to, a magnetic stirrer, an agitator, a mixer, a blender, and the like. Any conventional mixing, blending and/or combining techniques can be used including, but not limited to, magnetically induced stirring methods, pumping, in line circulation, inline static mixer, multi-styled traditional vertical and/or side-mount mechanical agitators, ribbon-like blenders, and the like. As long as the potassium hydroxide, that is introduced into the solution containing the cesium sulfate (and/or rubidium sulfate), reacts with the cesium sulfate (and/or rubidium sulfate) present, the mixing or addition of the potassium hydroxide is sufficient for purposes of the present invention. For purposes of the present invention, the term "adding" includes adding potassium hydroxide to the solution that contains the cesium sulfate (and/or rubidium sulfate), or adding the solution that contains the cesium sulfate (and/or rubidium sulfate) to the potassium hydroxide.

With regard to the temperature that is used in the method to preferentially precipitate potassium sulfate, the temperature of the solution containing the cesium sulfate (and/or rubidium sulfate) can be any temperature above freezing to the boiling temperature of the solution, and is preferably at least 50° C. This temperature is the temperature of the solution containing the cesium sulfate (and/or rubidium sulfate). The elevated temperature of at least 50° C., if used, can be achieved prior to the addition of the potassium hydroxide, or it can be achieved during the addition of the potassium hydroxide, or it can be achieved after addition of the potassium hydroxide. This temperature of at least 50° C. can be from about 50° C. to the boiling point of the solution containing the cesium sulfate (and/or rubidium sulfate). The maintaining of this temperature for the solution containing the cesium sulfate (and/or rubidium sulfate), once the potassium hydroxide is present and dissolved or dispersed or mixed in the solution containing the cesium sulfate (and/or rubidium sulfate), is generally until the potassium sulfate precipitate is formed and, preferably, is held at this temperature until most or all of the potassium sulfate precipitate is formed or that is capable of forming due to solubility limits, which can be on the order of seconds to minutes.

As an option, the causing of the potassium sulfate precipitate to form can be done in one or more stages to more efficiently and preferentially cause the formation of the potassium sulfate precipitate versus the formation of other precipitates, such as cesium sulfate precipitate (and/or rubidium sulfate precipitate). The reaction can be done in stages where the solution with the cesium sulfate (and/or rubidium sulfate) present is raised to a temperature of from about 50° C. to the boiling point of the blend to cause formation of just the potassium sulfate precipitate (a first stage). At this point, as an option, the temperature can be lowered to below 50° C. (e.g., cool the blend) and remove or separate the thus-formed potassium sulfate precipitate from the solution.

For any of the methods of the present application, the removal of the potassium sulfate precipitate can be done by any standard filtering or removal techniques, such as membranes, filter pads, filter paper, and the like.

For any of the methods of the present invention, the percentage (in wt %) of precipitate removed can be from about 1% to 100% of the precipitate present and preferably at least about 25%, at least about 50%, at least about 75%, at least about 85%, at least about 90%, at least about 95%, at least about 99% of the precipitate (based on the amount of precipitate present) can be removed.

The lowering of the temperature to below 50° C. can be done through any temperature reduction technique, such as an ice bath, water jacket, other cooling jackets, and the like. Then, the solution (e.g., with removed potassium sulfate precipitate) can be elevated to a temperature of from about 50° C. to the boiling temperature of this solution (that had precipitate removed) to remove water from this solution which causes the reduction in solubility of any remaining potassium sulfate to further occur (a second stage) and thus result in additional potassium sulfate precipitate. For instance, at this second stage of temperature elevation, the percent water in solution can be from about 20 wt % to about 80 wt %, and by boiling, can be reduced to from about 50 wt % to about 20 wt % water, based on the weight of the solution (that had the precipitate removed). Then, after this formation of additional potassium sulfate precipitate, the solution can be reduced in temperature to below 50° C., to again remove the precipitate using the same removal or separating techniques as above.

Afterwards, the solution can optionally be subjected again to elevated temperatures, such as from about 50° C. to the boiling point of the solution with precipitate removed (a third stage), and preferably boiled again or subjected to temperatures to cause boiling and thus remove more water (e.g., reduce water content) from the solution so as to ensure that any remaining potassium sulfate can fall out of solution and form a potassium sulfate precipitate. Again, by boiling to remove further water (e.g., reduce water content), the solubility of the potassium sulfate becomes more conducive to the potassium sulfate precipitate forming. At this point, for the removal of additional potassium sulfate precipitate, the percent water in solution can be from about 40 wt % to about 20 wt %.

Thus, with this process, the method can further comprise removing water (e.g., reducing water content) from the solution in order to precipitate additional potassium sulfate and then involves separating at least a portion of the additional potassium sulfate precipitate from the solution, and these steps can be optionally repeated one or more times, such as two times, three times, four times, or five or more times in order to ensure that the potassium sulfate precipitate is removed to its desired or fullest extent.

While the solution containing the cesium sulfate (and/or rubidium sulfate) can be raised to a temperature of at least 50° C. prior to, during, or after addition of the potassium hydroxide, to maximize the amount of the potassium sulfate precipitate and minimize precipitates that contain cesium (and/or rubidium), it is preferred to have the solution containing the cesium sulfate (and/or rubidium sulfate) at a temperature of about 50° C. or higher before addition of the potassium hydroxide. In general, this optional elevation of temperature for the solution containing the cesium sulfate (and/or rubidium sulfate) can be a temperature of from about 50° C. to the boiling point of the solution containing the cesium sulfate (and/or rubidium sulfate). Depending on the particular amount of cesium sulfate (and/or rubidium sulfate) in solution and purity of the solution, this boiling temperature can be from about 105° C. to about 115° C., such as from about 105° C. to about 110° C., or from about 107° C. to about 110° C. The boiling point for this solution containing the cesium sulfate (and/or rubidium sulfate) depends upon the amount of cesium sulfate (and/or rubidium sulfate) present, the amount of water present, and/or other salts and/or additives that may be present.

For purposes of the present invention, the addition of the potassium hydroxide to the solution containing the cesium sulfate (and/or rubidium sulfate) can occur at temperatures below 50° C., such as from about 15° C. to about 50° C. and achieve the purposes of the present invention, which is to convert at least a portion of a cesium sulfate (and/or rubidium sulfate), and preferably most or all, to cesium hydroxide (and/or rubidium hydroxide). When using lower temperatures, such as below about 50° C., the ability of the potassium hydroxide to react with the cesium sulfate (and/or rubidium sulfate) and preferentially precipitate potassium sulfate decreases. Put another way, the more efficient process, so as to increase the amount of potassium sulfate precipitate and/or decrease or avoid any cesium sulfate precipitate (and/or rubidium sulfate precipitate), is to operate at temperatures of about 50° C. or higher. Temperatures that are higher are more preferred, meaning temperatures at or near the boiling point of the solution containing the cesium sulfate (and/or rubidium sulfate).

With regard to separating at least a portion of the sulfate precipitate from the solution, this can be done at elevated temperatures or at a lower temperature, such as ambient temperatures, such as from about 20° C. to about 25° C. If the solution is at an elevated temperature, then after the sulfate precipitate has formed, the solution can be reduced in temperature (e.g., cooled) or can remain at this elevated temperature for the separating step. Preferably, reducing the elevated temperature in a controlled fashion to a temperature below 50° C. is preferred. By having controlled cooling or a temperature profile, this permits an orderly crystallization of the salt from solution and, further, permits the crystallization to occur in the order of the metal salt's solubility. In other words, with orderly crystallization or an orderly reduction of temperature or step-wise reduction in temperature, this permits crystallization to occur in an orderly fashion such that the potassium sulfate precipitate crystallizes preferentially since its solubility is lower at each temperature compared to the cesium salt and/or rubidium salt. Thus, preferably, a rapid reduction in temperature is not preferred. For instance, a temperature reduction of 5° C. (or less) per minute can lead to orderly crystallization and a more orderly crystallization can occur at a temperature reduction of about 3° C. (or less) per minute, and an even more orderly crystallization can occur at a temperature reduction of about 1° C. (or less) per minute, and an even more orderly crystallization can occur at a temperature reduction of 0.5° C. (or less) per minute or a temperature reduction of 0.1° C. (or less) per minute. In other words, the slower the controlled cooling (or the slower the ΔT per minute), the more orderly the crystallization and the more preferential the potassium sulfate precipitates versus the precipitation of other salts, such as cesium and/or rubidium.

Preferably, a temperature of about 50° C. or higher is used for purposes of reacting the cesium sulfate (and/or rubidium sulfate) with the potassium hydroxide, as this higher temperature makes the alkali metal salts more soluble, but relatively speaking, the cesium salt (and/or rubidium salt) increases in solubility a lot more than and the potassium salt is not as soluble at this higher temperature, and, thus, this will lead to the preferential precipitation of the potassium sulfate. Then, by cooling in a controlled fashion, this keeps the potassium precipitate out of solution and drives out even more potassium precipitate as the temperature is controllably lowered so as to permit the orderly crystallization of the less soluble salts, namely potassium sulfates. Thus, an orderly decline of temperature preferentially permits more potassium sulfate to precipitate first, and this can continue with each controlled reduction in temperature. By using this preferred process, the very preferential precipitation of potassium sulfate (and if present, sodium sulfate precipitate and/or lithium sulfate precipitate) is achieved with little to none of the cesium precipitating (and/or rubidium precipitating) and, thus, remaining in solution for cesium hydroxide (and/or rubidium hydroxide) recovery.

With regard to the step of removing (e.g., reducing) water by heating or other techniques, as stated, removing water (e.g., reducing water content) alters the solubility of the salts present in solution. Thus, if the solution was raised to an elevated temperature at or near the boiling point of the solution containing the cesium sulfate (and/or rubidium sulfate) for the precipitation reaction of cesium sulfate (and/or rubidium sulfate) with the potassium hydroxide, this simultaneously removes some of the water. After the first separating of the potassium sulfate precipitate from the solution to obtain a solution with removed precipitate, the removing (e.g., reducing) of water from the solution can occur by re-heating the solution to near boiling or boiling. Typically, the temperature for this boiling point can actually be higher since the solubility changes due to a lower weight percent of water, and lower weight percent potassium salt in solution.

It is optional and possible to remove additional potassium sulfate precipitate by raising the temperature to about 50° C. to the boiling point of the solution, but more effective results with regard to achieving additional potassium sulfate precipitate formation can occur at higher temperatures near or at the boiling point of the solution that contains any remaining cesium sulfate (and/or rubidium sulfate)/potassium hydroxide.

If the solution containing the cesium sulfate (and/or rubidium sulfate) is subjected to elevated temperatures, such as 50° C. or higher (e.g., up to the boiling point of the solution), this temperature can be held for any length of time, but, in general, only a few seconds to minutes are needed for the potassium sulfate precipitate to preferentially form.

For purposes of this method to convert cesium sulfate to cesium hydroxide, the same method and steps and parameters can be applied to convert rubidium sulfate to rubidium hydroxide and can be applied to convert a mixture of rubidium sulfate/cesium sulfate to rubidium hydroxide/cesium hydroxide.

In this hydroxide conversion method(s), the cesium hydroxide (and/or rubidium hydroxide) can then optionally be converted to other cesium bearing salts (and/or other rubidium bearing salts). For instance, with the addition of formic acid, the cesium hydroxide in solution can be converted to cesium formate in solution (and water). Similarly, the rubidium hydroxide can be converted to rubidium formate.

Figure 6:
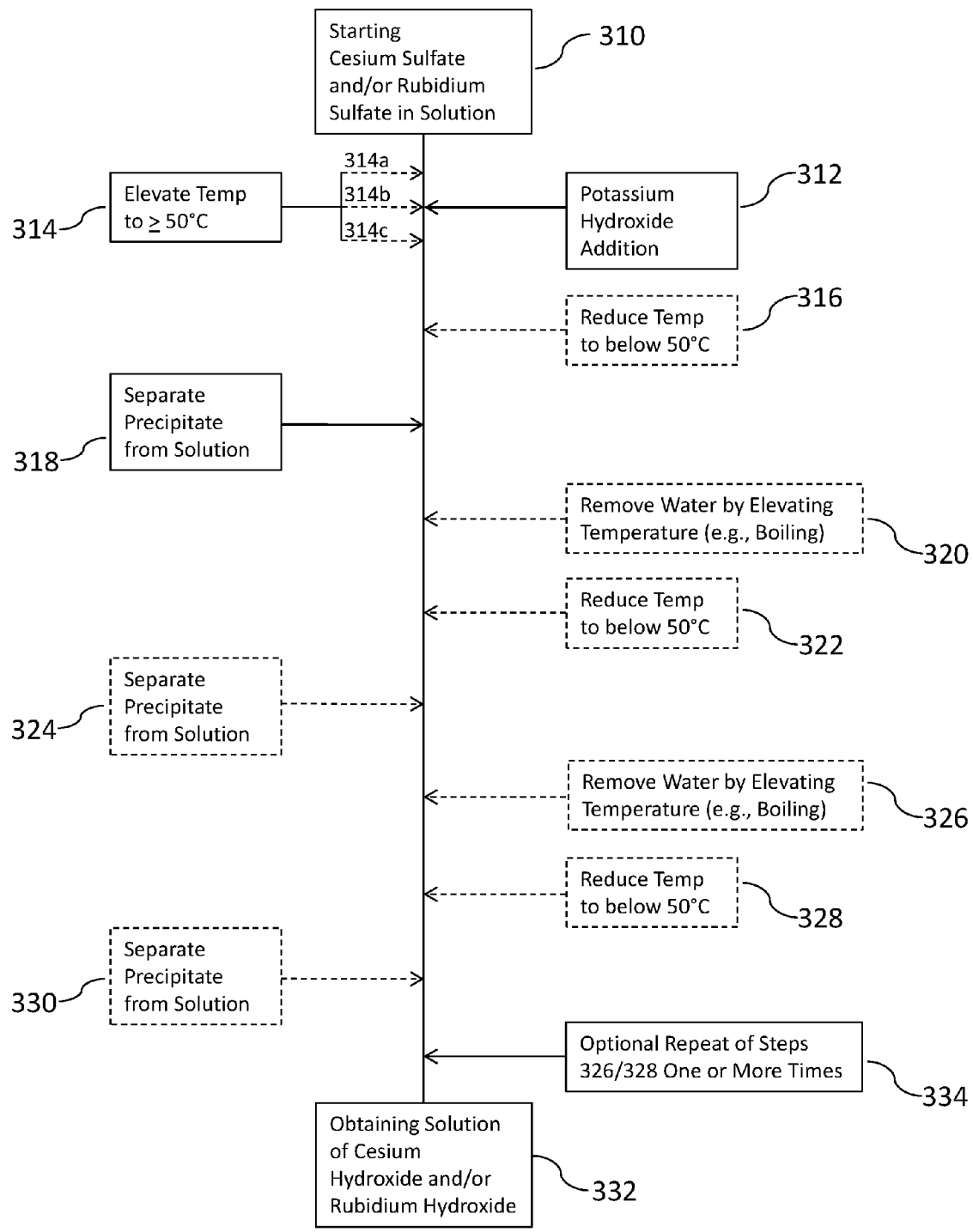

FIG. 6 is a flow chart summarizing steps and optional steps that can be used in the method to convert cesium sulfate and/or rubidium sulfate to cesium hydroxide/rubidium hydroxide, using the potassium hydroxide addition. Specifically, a sequence of steps is shown for this one preferred process with optional steps being presented in dash lines. A starting cesium sulfate and/or rubidium sulfate in solution 310 is used and potassium hydroxide is added to this solution in the potassium hydroxide addition step 312. Optionally, the temperature of the solution from step 310 can be elevated in step 314 either before (step 314A), during (step 314B), and/or after (step 314C) of the potassium hydroxide addition step 312. Then, if an elevated temperature is used, this temperature can be reduced to below 50° C. in step 316 using cooling jackets or other temperature reduction techniques. The precipitate, namely the potassium sulfate precipitate, can then be separated from solution in step 318 using standard separation techniques, such as filtering and the like. Then, in optional step 320, water can be removed (e.g., water content reduced) from this purified solution formed after step 318 by elevating the temperature, such as to a near boiling or boiling temperature for a period of time. If this step is used, then in step 322, the temperature can be reduced to below 50° C., and then in step 324, the further precipitate, namely potassium sulfate precipitate, can again be separated from this solution in step 324. Then, optionally, in step 326, further water can be removed by elevating the temperature of this converted solution from step 324 by elevating the temperature to preferably near a boiling or boiling point of this solution for a period of time. Then, after step 326, in step 328, the temperature can again be reduced to below 50° C. as an option using standard temperature reduction techniques, such as cooling jackets or plates. Then, after step 328, in step 330, this further precipitate, namely potassium sulfate precipitate that has formed during this optional step 326/328 can be removed in step 330 using the same removal techniques, such as filtration. Then, in step 334, the optional steps of 326 and 328 can optionally be repeated one or more times. Then, in step 332, a converted solution of cesium hydroxide and/or rubidium hydroxide is obtained. As indicated earlier, the removal of the precipitate can occur at any temperature, even at elevated temperatures, but it is more desirable and efficient to separate the precipitate from solution at a temperature of below 50° C.

In FIG. 7, a preferred method to convert cesium sulfate and/or rubidium sulfate to cesium hydroxide/rubidium hydroxide, using the potassium hydroxide addition is described. Further, the 3-stage process is identified and can be used in this method. Stage 1 can be used without Stage 2 and/or Stage 3. In other words, like FIG. 5, a one-step/stage process can be used. In FIG. 7, a starting cesium sulfate and/or rubidium sulfate in solution is used and shown at step 400. Then, the temperature of this starting solution (400) is raised to a near boiling or boiling temperature in step 402. Then, in step 404, potassium hydroxide is added to the solution at elevated temperature (above 50° C. to boiling temperature). Afterwards, in step 406, the controlled cooling of the solution to below 50° C. occurs in step 406, such as using a cooling jacket. Then, in step 408, the precipitate, namely the potassium sulfate precipitate (which can include, if present, lithium sulfate precipitate and/or sodium sulfate precipitate), is separated from the solution. Then, in step 410, the temperature of this solution from step 408 is elevated again to a near boiling or boiling temperature. Then, in step 412, the controlled cooling of this solution occurs, where the controlled cooling brings the solution down to a temperature below 50° C. In step 414, the further precipitate that has formed is then separated from solution. Then, in step 416, the temperature of this solution resulting from step 414 is then elevated again to a near boiling or boiling temperature of the solution. Then, in step 418, controlled cooling of this solution occurs to a temperature of below 50° C. Then, in step 420, any further precipitate that is formed is again separated from this solution to result in a purified solution of cesium hydroxide and/or rubidium hydroxide in step 422. In FIG. 7, stage 1 (424), stage 2 (426), and stage 3 (428) are shown.

For any of the methods of the present invention that involve recovering at least a portion of cesium formate and/or rubidium formate from a mixed alkali metal formate blend in solution, the method(s) can optionally include adding potassium hydroxide to the mixed alkali metal formate blend. The potassium hydroxide can be additionally added before, at the same time, and/or after the adding of the cesium sulfate, rubidium sulfate, cesium carbonate, cesium bicarbonate, rubidium carbonate, and/or rubidium bicarbonate. By adding the potassium hydroxide, cesium hydroxide, rubidium hydroxide or both additional forms. This method can further include (as an option) adding formic acid to the purified solution to convert at least a portion of the cesium hydroxide, rubidium hydroxide, or both to cesium formate, rubidium formate, or both, respectively. Obviously, if rubidium is present as rubidium hydroxide, at least a portion is converted to rubidium formate, and/or if cesium is present as cesium hydroxide, at least a portion is converted to cesium formate.

The potassium hydroxide can be added in an amount to form cesium hydroxide, rubidium hydroxide, or both, which is present in the purified solution so as to raise the pH of the purified solution, for instance, to raise the solution at least 1 pH unit by the addition of cesium hydroxide, rubidium hydroxide or both, or to raise it by about 1 pH unit to about 5 pH units by the addition cesium hydroxide, rubidium hydroxide or both. Generally, when the potassium hydroxide method is used in combination with one of the other methods (namely, the sulfate addition or carbonate/bicarbonate addition), additional cesium sulfate and/or rubidium sulfate and/or cesium carbonate and/or cesium bicarbonate and/or rubidium carbonate and/or rubidium bicarbonate can be added beyond what would be used. For instance, an additional 1 wt % to 50 wt % of the sulfate and/or carbonate can be used so that this extra amount is present to react with the potassium hydroxide and form cesium hydroxide and/or rubidium hydroxide besides the other products (namely, the cesium and/or rubidium formates). Generally, an additional amount of the sulfate and/or carbonate can be added to match or almost match (within 20% or within 10% or within 5%) the molar amounts of hydroxide added (from the potassium hydroxide).

For any of the methods of the present invention, when the boiling point of a solution or substance is mentioned, it is understood that the boiling point includes the initial boiling point and temperatures that exceed this initial boiling point, which can sometimes be at least 1° C. or more, to 10° C. to 15° C. to 25° C. to 40° C. or even more above the initial boiling point. Near boiling point can be within 10 to 15° C. of the initial boiling point.

For any of the methods of the present invention, the heating, removal of water, evaporation and/or attaining higher boiling points and solution densities mentioned herein and throughout the various steps and/or various method of the present invention are accomplished using any conventional techniques including, but not limited to, varied internal and/or external, direct and/or indirect heat exchangers like coils, bayonet style, U tube, inline style and/or jacketed, as well, crystallizers, evaporators, whether conducted at atmospheric, under vacuum, or at pressure conditions, respectively. Also, any heat input, if required, can use mediums such as boiler generated steam, hot oil, and/or electrical resistance heating, and the like.

For any of the methods of the present invention, the cooling or removal of heat, as desired, can be achieved by evaporative cooling to ambient, or can be accomplished using any conventional technique including, but not limited to, varied heat exchangers such as coils, bayonet, U tube, panel coils, jacketed vessels, and the like. This cooling or removal heat can use or include inline, internal, external, direct, and/or indirect heat exchangers, and can be conducted under atmospheric, vacuum, and/or pressure conditions, respectively. Also, wherein the cooling media, if required, may include mediums, such as, cooling water, appropriate refrigeration fluids, and the like.

For any of the methods of the present invention, a temperature "below 50° C." can be a temperature of from just above the freezing point of the solution to 49.9° C., and for instance can be from 10° C. to 49.9° C., or from 10° C. to 45° C., or from 10° C. to 40° C., or from 10° C. to 30° C., or from 15° C. to 30° C., or from 20° C. to 30° C., or from 15° C. to 25° C., and the like.

For any of the methods of the present invention, the reference to "a few seconds to minutes" for precipitation to occur can be 1 second to 1 hour or more, such as 1 second to 45 minutes, or 1 second to 30 minutes, or 1 second to 15 minutes, or 1 second to 10 minutes, or 1 second to 5 minutes, or 1 second to 60 seconds, or 5 seconds to 75 seconds, or 10 seconds to 75 seconds, or 15 seconds to 100 seconds, or 30 seconds to 100 seconds, and the like.

For any of the methods of the present invention, the reference to "solubility," projected solubility, or wt % in solution is a reference to solubility of the salt (e.g., cesium salt) at from about 15° C. to about 30° C. The solubility will be higher at higher temperatures. However, as indicated in the present invention, the solubility of some alkali metals (e.g., cesium and rubidium) can increase a lot more at higher temperatures than other alkali metals (e.g., potassium, sodium, and/or lithium) at the same increased temperature.

The present invention includes the following aspects/embodiments/features in any order and/or in any combination:

1. A method to recover at least a portion of cesium formate from a mixed alkali metal formate blend in solution comprising cesium formate and potassium formate, said method comprising:
   adding cesium sulfate to said mixed alkali metal formate blend to form potassium sulfate precipitate and additional cesium formate in said solution; and
   separating at least a portion of said potassium sulfate precipitate from said solution to obtain a purified solution.

2. The method of any preceding or following embodiment/feature/aspect, further comprising a) reducing water content from said purified solution in order to precipitate additional potassium sulfate and b) separating at least a portion of said additional potassium sulfate precipitate from said purified solution, and optionally repeating a) and b) one or more times.

3. The method of any preceding or following embodiment/feature/aspect, wherein said removing water is achieved by heating said purified solution.

4. The method of any preceding or following embodiment/feature/aspect, wherein said repeating of a) and b) occurs at least once and said removing water is achieved by heating.

5. The method of any preceding or following embodiment/feature/aspect, wherein said alkali metal formate blend is at a temperature or raised to a temperature of about 50° C. or higher, so as to preferentially precipitate potassium sulfate precipitate and form additional cesium formate in said solution.

6. The method of any preceding or following embodiment/feature/aspect, further comprising a) heating said purified solution to a temperature of from about 50° C. to boiling point of said purified solution in order to reduce water content and precipitate additional potassium sulfate and b) separating at least a portion of additional potassium sulfate precipitate from said purified solution, and repeating a) and b) at least once.

7. The method of any preceding or following embodiment/feature/aspect, wherein said mixed alkali metal formate blend in solution comprises from about 1 wt % to about 99 wt % cesium formate and from about 99 wt % to 1 wt % potassium formate based on the weight of alkali metal formates present in said blend.

8. The method of any preceding or following embodiment/feature/aspect, wherein said mixed alkali metal formate blend in solution comprises from about 20 wt % to about 60 wt % cesium formate and from about 80 wt % to about 40 wt % potassium formate based on the weight of alkali metal formates present in said blend.

9. The method of any preceding or following embodiment/feature/aspect, wherein said mixed alkali metal formate blend in solution comprises from about 30 wt % to about 45 wt % cesium formate and from about 70 wt % to about 55 wt % potassium formate based on the weight of alkali metal formates present in said blend.

10. The method of any preceding or following embodiment/feature/aspect, wherein said cesium sulfate is added in an amount to react with from about 10 wt % to 100 wt % of potassium formate present in said blend.

11. The method of any preceding or following embodiment/feature/aspect, wherein said cesium sulfate is added in an amount to react with from 50 wt % to 95 wt % of potassium formate present in said blend.

12. The method of any preceding or following embodiment/feature/aspect, wherein said cesium sulfate is added in an amount to react with from 90 wt % to 95 wt % of potassium formate present in said blend.

13. The method of any preceding or following embodiment/feature/aspect, wherein said cesium sulfate is added as one addition to said blend.

14. The method of any preceding or following embodiment/feature/aspect, wherein said cesium sulfate is added as multiple additions at separate times to said blend.

15. The method of any preceding or following embodiment/feature/aspect, wherein said adding is continuous, semi-continuous, or by single addition prior to said separating.

16. The method of any preceding or following embodiment/feature/aspect, wherein said method is conducted in the absence of a barium compound.

17. The method of any preceding or following embodiment/feature/aspect, wherein said purified solution has a specific gravity of from about 1.6 to about 2.3 s.g. at 25° C.

18. The method of any preceding or following embodiment/feature/aspect, wherein said purified solution, after said steps a) and b), has a specific gravity of from about 2 to about 2.3 s.g. at 25° C.

19. The method of any preceding or following embodiment/feature/aspect, wherein said purified solution has a specific gravity of from about 2 to about 2.3 s.g. at 25° C.

20. The method of any preceding or following embodiment/feature/aspect, wherein said purified solution, after said steps a) and b), has a specific gravity of from about 2.2 to about 2.3 s.g. at 25° C.

21. The method of any preceding or following embodiment/feature/aspect, wherein said purified solution has sulfate levels of 16,000 ppm or less.

22. The method of any preceding or following embodiment/feature/aspect, wherein said purified solution has sulfate levels of 8,000 ppm or less.

23. The method of any preceding or following embodiment/feature/aspect, wherein said purified solution has sulfate levels of 2,400 ppm or less.

24. The method of any preceding or following embodiment/feature/aspect, wherein said purified solution has sulfate levels of 1,200 ppm or less.

25. The method of any preceding or following embodiment/feature/aspect, wherein said purified solution has sulfate levels of 600 ppm or less.

26. The method of any preceding or following embodiment/feature/aspect, further comprising adding potassium hydroxide to said mixed alkali metal formate blend, wherein said potassium hydroxide is added before, at the same time, or after said adding of said cesium sulfate.

27. The method of any preceding or following embodiment/feature/aspect, wherein cesium hydroxide additionally forms, and said method further comprises adding formic acid to said purified solution to convert at least a portion of said cesium hydroxide to cesium formate.

28. The method of any preceding or following embodiment/feature/aspect, wherein said potassium hydroxide is added in an amount to form cesium hydroxide which is present in said purified solution so as to raise the pH of the purified solution.

29. The method of any preceding or following embodiment/feature/aspect, wherein said pH is raised at least 1 pH unit by the cesium hydroxide.

30. The method of any preceding or following embodiment/feature/aspect, wherein said pH is raised from about 1 pH unit to about 5 pH units by the cesium hydroxide.

31. The method of any preceding or following embodiment/feature/aspect, further comprising pre-treating said mixed alkali formate blend to remove non-formate material other than water, by filtering or raising the pH of the mixed alkali metal formate blend.

32. A method to recover at least a portion of cesium formate or rubidium formate or both, from a mixed alkali metal formate blend in solution comprising component 1) cesium formate or rubidium formate or both and component 2) potassium formate, lithium formate, or sodium formate, or any combination thereof, said method comprising:
adding cesium sulfate or rubidium sulfate or both to said mixed alkali metal formate blend to form an alkali metal sulfate precipitate from the alkali metal of component 2) and additional cesium formate or rubidium formate or both in said solution; and
separating at least a portion of said alkali metal sulfate precipitate from said solution to obtain a purified solution.

33. The method of any preceding or following embodiment/feature/aspect, further comprising a) reducing water content from said purified solution in order to precipitate additional alkali metal sulfate and b) separating at least a portion of said additional alkali metal sulfate precipitate from said purified solution, and optionally repeating a) and b) one or more times.

34. The method of any preceding or following embodiment/feature/aspect, wherein said removing water is achieved by heating said purified solution.

35. The method of any preceding or following embodiment/feature/aspect, wherein said repeating of a) and b) occurs at least once and said removing water is achieved by heating.

36. The method of any preceding or following embodiment/feature/aspect, wherein said alkali metal formate blend is at a temperature or raised to a temperature of about 50° C. or higher, so as to preferentially precipitate an alkali metal sulfate precipitate from the alkali metal of component 2) and form additional cesium formate or rubidium formate or both in said solution.

37. The method of any preceding or following embodiment/feature/aspect, further comprising adding potassium hydroxide to said mixed alkali metal formate blend, wherein said potassium hydroxide is added before, at the same time, or after said adding of said cesium sulfate, rubidium sulfate or both.

38. The method of any preceding or following embodiment/feature/aspect, wherein cesium hydroxide, rubidium hydroxide or both additionally forms, and said method further comprises adding formic acid to said purified solution to convert at least a portion of said cesium hydroxide, rubidium hydroxide, or both to cesium formate, rubidium formate, or both, respectively.

39. The method of any preceding or following embodiment/feature/aspect, wherein said potassium hydroxide is added in an amount to form cesium hydroxide, rubidium hydroxide, or both, which is present in said purified solution so as to raise the pH of the purified solution.

40. The method of any preceding or following embodiment/feature/aspect, wherein said pH is raised at least 1 pH unit by the cesium hydroxide, rubidium hydroxide or both.

41. The method of any preceding or following embodiment/feature/aspect, wherein said pH is raised from about 1 pH unit to about 5 pH units by the cesium hydroxide, rubidium hydroxide or both.

42. A method to recover at least a portion of cesium formate from a mixed alkali metal formate blend in solution comprising cesium formate and potassium formate, said method comprising:
adding cesium carbonate or cesium bicarbonate or both to said mixed alkali metal formate blend to form potassium carbonate precipitate or potassium bicarbonate precipitate or both and additional cesium formate in said solution; and
separating at least a portion of said potassium carbonate precipitate or potassium bicarbonate precipitate or both from said solution to obtain a purified solution.

43. The method of any preceding or following embodiment/feature/aspect, wherein said alkali metal formate blend is at a temperature or raised to a temperature of about 50° C. or higher, so as to preferentially precipitate potassium carbonate precipitate or potassium bicarbonate precipitate or both and form additional cesium formate in said solution.

44. The method of any preceding or following embodiment/feature/aspect, further comprising a) reducing water content from said purified solution in order to precipitate additional potassium carbonate or potassium bicarbonate or both and b) separating at least a portion of said additional potassium carbonate precipitate or potassium bicarbonate precipitate or both from said purified solution, and optionally repeating a) and b) one or more times.

45. The method of any preceding or following embodiment/feature/aspect, wherein said removing water is achieved by heating said purified solution.

46. The method of any preceding or following embodiment/feature/aspect, wherein said repeating of a) and b) occurs at least once and said removing water is achieved by heating.

47. The method of any preceding or following embodiment/feature/aspect, wherein said temperature is from about 50° C. to boiling point of said mixed alkali formate blend in solution.

48. The method of any preceding or following embodiment/feature/aspect, further comprising adding water and formic acid to said potassium carbonate precipitate or potassium bicarbonate precipitate or both that is separated to form potassium formate in solution.

49. The method of any preceding or following embodiment/feature/aspect, further comprising adding potassium hydroxide to said mixed alkali metal formate blend, wherein said potassium hydroxide is added before, at the same time, or after said adding of said cesium carbonate or cesium bicarbonate or both.

50. The method of any preceding or following embodiment/feature/aspect, wherein cesium hydroxide additionally forms, and said method further comprises adding formic acid to said purified solution to convert at least a portion of said cesium hydroxide to cesium formate.

51. The method of any preceding or following embodiment/feature/aspect, wherein said potassium hydroxide is added in an amount to form cesium hydroxide which is present in said purified solution so as to raise the pH of the purified solution.

52. The method of any preceding or following embodiment/feature/aspect, wherein said pH is raised at least 1 pH unit by the cesium hydroxide.

53. The method of any preceding or following embodiment/feature/aspect, wherein said pH is raised from about 1 pH unit to about 5 pH units by the cesium hydroxide.

54. A method to recover at least a portion of cesium formate or rubidium formate or both from a mixed alkali metal formate blend in solution comprising component 1) cesium formate or rubidium formate or both and component 2) potassium formate, lithium formate, or sodium formate, or any combination thereof, said method comprising adding cesium carbonate, cesium bicarbonate, rubidium carbonate, or rubidium bicarbonate, or any combination thereof, to said mixed alkali metal formate blend to form an alkali metal carbonate precipitate or alkali metal bicarbonate precipitate or both from the alkali metal of component 2), and form additional cesium formate or rubidium formate or both in said solution; and separating at least a portion of said alkali metal carbonate precipitate or alkali metal bicarbonate precipitate from said solution to obtain a purified solution.

55. The method of any preceding or following embodiment/feature/aspect, wherein said alkali metal formate blend is at a temperature or raised to a temperature of about 50° C. or higher, so as to preferentially precipitate said alkali metal carbonate precipitate or alkali metal bicarbonate precipitate or both, and form additional cesium formate, rubidium formate or both in said solution.

56. The method of any preceding or following embodiment/feature/aspect, further comprising adding potassium hydroxide to said mixed alkali metal formate blend, wherein said potassium hydroxide is added before, at the same time, or after said adding of said cesium carbonate, cesium bicarbonate, rubidium carbonate, or rubidium bicarbonate, or any combination thereof.

57. The method of any preceding or following embodiment/feature/aspect, wherein cesium hydroxide, rubidium hydroxide or both additionally forms, and said method further comprises adding formic acid to said purified solution to convert at least a portion of said cesium hydroxide to cesium formate, or at least a portion of said rubidium hydroxide to rubidium formate, or both.

58. The method of any preceding or following embodiment/feature/aspect, wherein said potassium hydroxide is added in an amount to form cesium hydroxide, rubidium hydroxide or both, which is present in said purified solution so as to raise the pH of the purified solution.

59. The method of any preceding or following embodiment/feature/aspect, wherein said pH is raised at least 1 pH unit by the cesium hydroxide, rubidium hydroxide, or both.

60. The method of any preceding or following embodiment/feature/aspect, wherein said pH is raised from about 1 pH unit to about 5 pH units by the cesium hydroxide, rubidium hydroxide, or both.

61. A method to convert at least a portion of cesium sulfate in solution to cesium hydroxide in said solution, said method comprising adding potassium hydroxide to said solution to form potassium sulfate precipitate and cesium hydroxide in said solution; and separating at least a portion of said potassium sulfate precipitate from said solution to obtain a resulting solution containing cesium hydroxide.

62. The method of any preceding or following embodiment/feature/aspect, further comprising a) reducing water content from said resulting solution in order to precipitate additional potassium sulfate and b) separating at least a portion of said additional potassium sulfate precipitate from said resulting solution, and optionally repeating a) and b) one or more times.

63. The method of any preceding or following embodiment/feature/aspect, wherein said removing water is achieved by heating said resulting solution.

64. The method of any preceding or following embodiment/feature/aspect, wherein said repeating of a) and b) occurs at least once and said removing water is achieved by heating.

65. The method of any preceding or following embodiment/feature/aspect, wherein said solution containing said cesium sulfate is at a temperature or raised to a temperature of about 50° C. or higher, so as to preferentially precipitate potassium sulfate precipitate and form cesium hydroxide in said solution.

66. The method of any preceding or following embodiment/feature/aspect, further comprising a) heating said resulting solution to a temperature of from about 50° C. to boiling point of said resulting solution in order to reduce water content and precipitate additional potassium sulfate and b) separating at least a portion of additional potassium sulfate precipitate from said resulting solution, and repeating a) and b) at least once.

67. The method of any preceding or following embodiment/feature/aspect, wherein said cesium sulfate in solution comprises from about 1 wt % to about 100 wt % cesium sulfate based on the weight of alkali metal salts present in said solution.

68. The method of any preceding or following embodiment/feature/aspect, wherein said cesium sulfate in solution comprises from about 60 wt % to about 99 wt % cesium sulfate based on the weight of alkali metal salts present in said solution.

69. The method of any preceding or following embodiment/feature/aspect, wherein said cesium sulfate in solution comprises from about 90 wt % to about 99 wt % cesium sulfate based on the weight of alkali metal salts present in said solution.

70. The method of any preceding or following embodiment/feature/aspect, wherein said potassium hydroxide is added in an amount to react with from about 10 wt % to 100 wt % of cesium sulfate present in said solution.

71. The method of any preceding or following embodiment/feature/aspect, wherein said potassium hydroxide is added in an amount to react with from 80 wt % to 99.5 wt % of cesium sulfate in said solution.

72. The method of any preceding or following embodiment/feature/aspect, wherein said potassium hydroxide is added in an amount to react with from 95 wt % to 99 wt % of cesium sulfate in said solution.

73. The method of any preceding or following embodiment/feature/aspect, wherein said potassium hydroxide is added as one addition to said solution.

74. The method of any preceding or following embodiment/feature/aspect, wherein said potassium hydroxide is added as multiple additions at separate times to said solution.

75. The method of any preceding or following embodiment/feature/aspect, wherein said adding is continuous, semi-continuous, or by single addition prior to said separating.

76. A method to convert at least a portion of cesium sulfate or rubidium sulfate or both in solution to cesium hydroxide or rubidium hydroxide or both in said solution, said method comprising adding potassium hydroxide to said solution to form potassium sulfate precipitate and cesium hydroxide or rubidium hydroxide or both in said solution; and separating at least a portion of said potassium sulfate precipitate from said solution to obtain a resulting solution containing cesium hydroxide or rubidium hydroxide or both.

77. The method of any preceding or following embodiment/feature/aspect, further comprising a) reducing water content from said resulting solution in order to precipitate additional potassium sulfate and b) separating at least a portion of said additional potassium sulfate precipitate from said resulting solution, and optionally repeating a) and b) one or more times.

78. The method of any preceding or following embodiment/feature/aspect, wherein said method is conducted in the absence of a barium compound.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be exemplary of the present invention.

EXAMPLES

Example 1

$Cs_2SO_4$ Route with Oil-Field Recovered Cs,K Formate Brine

A sample (of equal amount) was taken from each of ten totes of a returned 1.82 SG mixed Cs,K formate oil-field brine to make a combined sample for testing (referred to as the 'sample'). The brine had already been filtered. Confirmed by a sample measurement, the specific gravity of the sample was 1.82 SG. By volume, this suggested a blend of 39.6832% by volume of 2.20 SG Cs Formate solution, and 60.3168% by volume of 1.57 SG K Formate solution. Stock Cs Sulfate solution, nominally 50% by wt, with a 1.6758 SG and solution pH of 8.02 was chosen as the $Cs_2SO_4$ reactant solution.

(Stage 1) 200 ml of the mixed formate brine was added to a 500 ml glass beaker and placed on a heated stirrer plate. The agitated sample was heated to 80 to 100° C. While maintaining this temperature range, 125 ml of the cited stock Cs Sulfate solution was added. The wetted graduated cylinders to measure out the two solutions were flushed clean with clean water to ensure the amounts added were correct. The amount of water used for flushing was 45 ml, and was added into the reaction beaker.

The beaker reactants were allowed to heat to a solution boiling point of 109° C., and then allowed to cool on a second stirrer plate to 15 to 30° C., and then filtered to obtain a filtrate (purified solution). The results for this Stage 1 of the process were as follows:

SG of filtrate was 1.685, volume of filtrate was 310 ml, ppm $SO_4$ of filtrate was 11,513 ppm, crystal-like solids recovered were 43.84 grams, dry and crystalline powder in appearance for the precipitate, filtration of filtrate was fast and clear.

(Stage 2) The filtrate (purified solution) was further processed, similarly to that above, by heating the first stage filtrate to a boiling point of 125° C., and then allowing the brine to cool to 15 to 30° C. on a separate (unheated) stirrer plate, and then filtered. A further processed filtrate (further purified solution) was obtained. The results for this Stage 2 of the process were as follows:

SG of filtrate was 2.048, volume of filtrate was 178 ml, ppm $SO_4$ of filtrate was 3,027 ppm, starchy and crystal-like solids recovered were 27.31 grams, dry, starchy, crystalline powder in appearance for the precipitate, filtration of filtrate was fast and clear.

(Stage 3) The resulting filtrate (from Stage 2) was further processed, similarly to that above, by heating the second stage filtrate to a boiling point of 135° C., and then allowing the brine to cool to 15 to 30° C. on a separate (unheated) stirrer plate, and then filtered. A further processed filtrate (further purified solution) was obtained. The results for this Stage 3 of the process were as follows:

SG of filtrate was 2.251, $H_2O$ amount in filtrate was 25.218 wt %, volume of filtrate was 145 ml, ppm $SO_4$ of filtrate was 832 ppm, pH was about 10-11, ppm Li, Na, K, Rb, respectively, were 490 ppm, 16,080 ppm, 26,830 ppm, and 5,020 ppm, crystal-like solids were 3.24 grams, greasy, wax-like and powdered crystals in appearance for the precipitate, filtration of the filtrate was steady and clear.

Example 2

$Cs_2SO_4$ Route with a Lab Prepared Virgin Cs,K Formate Brine

In this Example, a Cs,K mixed formate brine is lab prepared in its virgin state, without addition of any oil-field additives. This removes the potential issue of additives precipitating during the Cs,K mixed brine separation and restoration process. A standard, buffered, mixed formate brine was prepared using virgin 2.20 SG Cesium Formate solution and a virgin 1.57 SG K-Formate solution. The 50:50 (% by volume) blend formulation was prepared for the separation and restoration trial.

125 ml Cs Formate and 125 ml K Formate were measured and mixed in a 500 ml glass Pyrex beaker, and placed on a heated and agitated stirrer plate. The blended formate brine measured 1.88 SG, as aligned with the blending tables.

Stock Industrial Grade 50 wt % Cs Sulfate solution was chosen for the trial. The 1.67 SG stock 50% Cs Sulfate solution contained about 140,000 ppm of Sulfate, including an accounting for the sulfate from other sulfate salts.

(Stage 1) Added to the 50:50 mixed formate blend, was 225 ml of the Cs Sulfate solution. The, now clouded, reactant solution mix was heated to its initial boiling point temperature of 110° C. The solution was then switched to another agitated stirrer plate, and allowed to cool to near room temperature of 15 to 30° C. When observed at room temperature, the precipitate appeared to be very fine powdery crystals that were easily suspended.

To separate the crystals from the aqueous phase, at near room temperature (about 25° C.), the slurry was vacuum filtered using filter funnel, flask, and #94 Ahlstrom filter paper. Filtration was quite fast and clear. The crystals were allowed to further de-water under vacuum, in situ, for about an additional 15 minutes.

The crystals were then dried by a lab furnace and measured for salt weight and % moisture. The dry weight was 91.76 grams. De-watering was excellent, as the entrained moisture content was only 3.20 wt %. The $K_2SO_4$ crystal weight expected for the yet completed entire trial was projected at 99.6 grams, dry weight. This initial reaction separated 92% (by weight) of this total.

The clear filtrate was assessed for specific gravity and ppm sulfate using a turbidimetric method. The filtrate density measured 1.70 SG. The ppm $SO_4$ measured about 3800 ppm.

(Stage 2) This filtrate was then heated to 125° C., using a similar set-up as previously described. When the target solution boiling point of 125° C. was achieved, the solution was cooled to 30 to 50° C. The approach taken for the agitated cool, from 125° C., was executed in a fashion similar to that previously described.

To separate the crystals from the aqueous phase, the slurry was vacuum filtered using filter funnel, flask, and #94 Ahlstrom filter paper. The warm slurry filtered clearly and steadily throughout filtration. The crystal residue was allowed to further de-water under vacuum, in situ, for about an additional 15 minutes.

The crystalline residue was then dried by lab furnace and measured for dry weight and % moisture. The wet weight was 7.34 grams. The dry weight was 6.70 grams. The cumulative dry weight totaled 98.3 grams. The clear filtrate was assessed for specific gravity, and ppm sulfate using a turbidimetric method. The filtrate density measured 2.02 SG. The $SO_4$ content measured about 1350 ppm.

(Stage 3) The filtrate was then heated to 137° C., using a similar set-up as previously described. When the target solution boiling point of 137° C. was achieved, the solution was cooled to 15 to 30° C. The approach taken for the agitated cool, from 137° C., was executed in a fashion similar to that previously described.

To separate the remaining residual turbidity (circa 300 ntus) from the aqueous phase, the liquor was vacuum filtered using a Millipore filter funnel, vacuum flask, and #131 filter paper. The cooled slurry filtered clearly, though less slowly than previously. The greasier crystalline residue was allowed to further de-water under vacuum, in situ, for an additional period to lessen the potential of lubricious high density brine entrainment.

The residue was quite minimal at <2 grams wet weight. The cumulative precipitate comprising $K_2SO_4$ aligned closely with the projections at the outset of the trial of 99.6 grams. The filtrate density of the restored Cs Formate Fraction was measured at 2.255 SG. The final filtrate volume recovered, when corrected from 2.255 SG to 2.20 SG, was 230.4 ml. The calculated/projected theoretical 2.20 SG filtrate volume for the Cs Formate fraction, based upon the cesium comprised input reactants, was 229.4 ml. Hence, separation and recovery were excellent. The ppm $SO_4$ of the final filtrate was measured at 770 ppm $SO_4$.

Example 3

$HCO_3/CO_3$ Route

In a 500 ml glass beaker, 200 ml of a mixed Cs, K Formate brine blend, returned from use in the oil field, was heated to 80° C. on an agitated heated stirrer plate. While maintaining a temperature of 80 to 100° C. throughout the addition, 60 ml of 2.3 SG 68 wt % $Cs_2CO_3$ solution was added to the beaker. The mixture was heated beyond its observed initial boiling point of 120° C., with increased heating to an intermediate boiling point of about 132° C. The sample was then agitated and cooled to 15 to 30° C. No filtering occurred (but could) but it was decided to heat further to achieve further precipitation. The solution was further heated, with agitation, to a boiling point of about 141.5° C. As done previously, the sample was allowed to cool on a separate agitated stirrer plate to near room temperature (about 25° C.), and then allowed to settle for observation of crystal bed level. A precipitate (solids phase) was observed, and appeared consistent with a potassium bicarbonate/carbonate precipitate.

To separate the aqueous phase from the solids phase, the slurry was vacuum filtered via funnel and filter flask using a #610 filter paper. The solution filtered quickly and clearly at room temperature, consistent with a potassium bicarbonate/carbonate precipitate. The powdery-like crystals were allowed to vacuum dry for about 15 minutes. The surface of the separated solids appeared quite dry, powdery and crystalline.

The filtered aqueous phase comprising the Cs Formate fraction measured 157 ml at 2.33 SG. The filtrate remained basic, between about 10 and 11 pH. The dry separated solids measured 31.23 grams. The filtered brine that contained the recovered Cs fraction was allowed to remain undisturbed for another week to ensure it remained stable as an aqueous solution, when exposed to nominal laboratory temperatures ranging from about 16 to 25° C.

A very minimal trace of dust, or powder-like, material, was observed after sitting for the week. The same as that observed after the first night of sitting. It possessed the same observed qualities of the solids from the 15 to 30° C. filtered primary fraction, with no loss in density. It was quickly and easily Millipore polish filtered using sub-micron paper, without incident, resulting in a minimal <0.1 g of net wet weight.

At 157 ml and 2.33 SG, the 2.20 SG ml equivalent of the Cs Formate fraction in the pre-separated 1.82 SG mixed formate brine blend of 80 ml, plus the contribution from the 60 ml of 68% $Cs_2CO_3$ solution of 58 ml, was 137 ml. Hence, the overall recovery of the high density Cs Formate comprised fraction was quite excellent. The expected weight of separated solids, if all precipitate were potassium bicarbonate, calculates to 28.79 grams of dry weight. This was consistent with the 60 ml of $Cs_2CO_3$ that was added.

Recovery of the potassium bicarbonate/carbonate solids fraction allows for restoration of this phase to the standard 1.57 SG K-Formate near saturated solution by simply adding formic acid and water to the powdery residue, as required. The reaction releases the carbonate phase as $CO_2$. This method enables a closed loop recovery system where the highly valued cesium atoms are contained, and fully recovered by the process, within the two respective cesium and potassium product fractions.

The recovery of the Cs Fraction from the 1.82 SG mixed brine plus the cesium carbonate added was near identical to that experienced with the separation and restoration process using cesium sulfate as the vehicle for separation and recovery.

Example 4

OH Route

There are times where pH is preferably manipulated higher to precipitate and remove oil-field additives. This process can be executed to extremely high pH's in concert with other separation and restoration methods, or by itself. The following illustrates the more extreme version of pH manipulation forming CsOH from Cs Sulfate and without use of the more expensive barium hydroxide, and like bases. The process uses potassium hydroxide. The following illustrates an example of a simplified two phase system using Cs Sulfate and mono-valent KOH.

In a two liter glass beaker was 1000 ml of a nominal 50% $Cs_2SO_4$ solution, or about the equivalent of 222 grams of contained ($SO_4$) sulfate. Using an agitated stirrer bar hot plate, this solution was heated to about 65° C. While maintaining a temperature of about 65° C. or higher, 396 ml of 1.45 SG, 45% KOH, or about 396 grams of contained (OH) hydroxide, was added to this two liter beaker. When this addition was completed, the solution was heated to its initial boiling point of about 106° C., and then beyond this, to a solution boiling point of about 112° C. The solution was then switched to another agitated stirrer plate to cool to near room temperature of 15 to 30° C.

The solution was filtered to separate the potassium sulfate crystals from the CsOH comprised mono-valent hydroxide aqueous phase. Vacuum filtration qualities were again exemplary, being fast and clear. The filter paper used was #610. Recovered, when separated, were 765 ml of 1.76 SG filtrate, and 405 net wet grams of sulfate crystals. The crystals were then dried to ascertain the % moisture entrained, believed to be quite minimal. This retained content measured 5 wt %. Vacuum (filtration) dewatering was purposely interrupted a bit earlier than normal, and additional vacuum displacement time would have further reduced this entrained moisture content.

The filtrate was analyzed for several key parameters, such as ppm K and $SO_4$, as well, actual outcomes against expected outcomes, more quantitatively. Overall, calculations of the CsOH solution fraction, realized a recovery >97% (by weight) of the cesium that was charged as Cs Sulfate.

The turbidimetric based sulfate present in the CsOH solution was measured to be only 10,400 ppm $SO_4$, despite adding about 222 g sulfate. The ppm K was analyzed at 14760 ppm, by wt, despite having charged about 181 g potassium. The % $H_2O$ in the CsOH solution, as measured by Karl Fisher titration, was 48.76 wt %.

The dry potassium sulfate salt precipitated and recovered as $K_2SO_4$ was 381 grams, versus a theoretical 399 grams $K_2SO_4$, had all of the sulfate salt added been precipitated and recovered as $K_2SO_4$.

These analyses and calculations implied that more KOH could have been charged in the original mixed alkali Sulfate and Hydroxide reaction, to extend and improve a refined one step reaction outcome. To refine this window further, an additional reaction was executed, where additional amount of KOH was charged to the primary CsOH filtrate cited above.

Example 5

OH Route Further Refined

Added to a one liter glass beaker was 565 ml of the above 1.756 SG CsOH solution recovered as the filtrate from the above reaction of Example 4. Using an agitated stirrer bar hot plate, this solution was heated to 80° C. While maintaining a temperature of 80° C. or higher, 22 ml of 1.456 SG, 45 wt % KOH was further added to this one liter beaker. When this addition was completed, the solution was heated to its initial boiling point of about 114° C., and then beyond this, to a solution boiling point of about 119° C. The solution was then switched to another agitated stirrer plate to cool to near room temperature of 15 to 30° C.

The solution was filtered to separate the potassium sulfate crystals from the CsOH monovalent hydroxide aqueous phase. Vacuum filtration qualities were again exemplary, being fast and clear. Filter paper #610 was used. Recovered, when separated, were 486 ml of 1.85 SG filtrate, and 24 net wet grams of sulfate crystals. The crystals were again quite dry, and similar to the initial primary filtered salt qualities, as previously cited and discussed. This was quite close to the expected $K_2SO_4$ (dry weight) precipitate of 22 grams.

The CsOH filtrate solution was further analyzed. Despite adding 22 ml of KOH, the net additional add of ppm K to this filtrate from the prior primary filtrate, was only a 900 ppm gain into this further concentrated CsOH filtrate, or now, to a level of 17,100 ppm K. Further, the ppm $SO_4$ of this further concentrated CsOH filtrate was further reduced, now to a level of 4800 ppm $SO_4$. The % $H_2O$ was 40.5 wt %. Hence, this filtered CsOH monovalent hydroxide solution concentration was now 59.5% by weight.

It is notable that for the considerable water content of the CsOH solution that the solubility of sulfate, as potassium sulfate, is quite low. So too, using $Cs_2SO_4$ as the bases of the separation and restoration process presents a low sulfate yielding product by process. It is also noted that the process extent to produce CsOH by this method could have been further extended, however, this example was intended as illustrative, and could be used in concert with the other restoration and separation processes.

Alternatively, it could also be regarded on its own merit, as a uniquely standalone process that can be used to convert $Cs_2SO_4$ to CsOH without the considerably cost and yield of disadvantaged processes that use barium hydroxide, and like non-monovalent based hydroxide type raw material and processes.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method to convert at least a portion of cesium sulfate in solution to cesium hydroxide in said solution, said method comprising adding potassium hydroxide to said solution to form potassium sulfate precipitate and cesium hydroxide in said solution; and separating at least a portion of said potassium sulfate precipitate from said solution to obtain a resulting solution containing cesium hydroxide.

2. The method of claim 1, further comprising a) reducing water content from said resulting solution in order to precipitate additional potassium sulfate and b) separating at least a portion of said additional potassium sulfate precipitate from said resulting solution, and optionally repeating a) and b) one or more times.

3. The method of claim 2, wherein said removing water is achieved by heating said resulting solution.

4. The method of claim 2, wherein said repeating of a) and b) occurs at least once and said removing water is achieved by heating.

5. The method of claim 1, wherein said solution containing said cesium sulfate is at a temperature or raised to a temperature of about 50° C. or higher, so as to preferentially precipitate potassium sulfate and form cesium hydroxide in said solution.

6. The method of claim 1, further comprising a) heating said resulting solution to a temperature of from about 50° C. to boiling point of said resulting solution in order to reduce water content and precipitate additional potassium sulfate and b) separating at least a portion of additional potassium sulfate precipitate from said resulting solution, and repeating a) and b) at least once.

7. The method of claim 1, wherein said cesium sulfate in solution comprises from about 1 wt % to about 100 wt % cesium sulfate based on the weight of alkali metal salts present in said solution.

8. The method of claim 1, wherein said cesium sulfate in solution comprises from about 60 wt % to about 99 wt % cesium sulfate based on the weight of alkali metal salts present in said solution.

9. The method of claim 1, wherein said cesium sulfate in solution comprises from about 90 wt % to about 99 wt % cesium sulfate based on the weight of alkali metal salts present in said solution.

10. The method of claim 1, wherein said potassium hydroxide is added in an amount to react with from about 10 wt % to 100 wt % of cesium sulfate present in said solution.

11. The method of claim 1, wherein said potassium hydroxide is added in an amount to react with from 80 wt % to 99.5 wt % of cesium sulfate in said solution.

12. The method of claim 1, wherein said potassium hydroxide is added in an amount to react with from 95 wt % to 99 wt % of cesium sulfate in said solution.

13. The method of claim 1, wherein said potassium hydroxide is added as one addition to said solution.

14. The method of claim 1, wherein said potassium hydroxide is added as multiple additions at separate times to said solution.

15. The method of claim 1, wherein said adding is continuous, semi-continuous, or by single addition prior to said separating.

16. A method to convert at least a portion of cesium sulfate or rubidium sulfate or both in solution to cesium hydroxide or rubidium hydroxide or both in said solution, said method comprising adding potassium hydroxide to said solution to form potassium sulfate precipitate and cesium hydroxide or rubidium hydroxide or both in said solution; and separating at least a portion of said potassium sulfate precipitate from said solution to obtain a resulting solution containing cesium hydroxide or rubidium hydroxide or both.

17. The method of claim 16, further comprising a) reducing water content from said resulting solution in order to precipitate additional potassium sulfate and b) separating at least a portion of said additional potassium sulfate precipitate from said resulting solution, and optionally repeating a) and b) one or more times.

18. The method of claim 1, wherein said method is conducted in the absence of a barium compound.

19. The method of claim 2, wherein said method is conducted in the absence of a barium compound.

20. The method of claim 16, wherein said method is conducted in the absence of a barium compound.

21. The method of claim 17, wherein said method is conducted in the absence of a barium compound.

* * * * *